US012458508B2

(12) United States Patent
Yoon et al.

(10) Patent No.: US 12,458,508 B2
(45) Date of Patent: Nov. 4, 2025

(54) EXPANDABLE INTERBODY FUSION DEVICE

(71) Applicant: CTL Amedica Corporation, Addison, TX (US)

(72) Inventors: Hongwon Yoon, Plano, TX (US); Jon Suh, Ambler, PA (US); Sean Suh, Milltown, NJ (US)

(73) Assignee: CTL BIOTEC, CORPORATION, Daegu (KR)

( * ) Notice: Subject to any disclaimer, the term of this patent is extended or adjusted under 35 U.S.C. 154(b) by 12 days.

(21) Appl. No.: 17/684,079

(22) Filed: Mar. 1, 2022

(65) Prior Publication Data

US 2022/0280309 A1 Sep. 8, 2022

Related U.S. Application Data

(63) Continuation of application No. 17/194,034, filed on Mar. 5, 2021, now Pat. No. 11,291,559.

(51) Int. Cl.
*A61F 2/44* (2006.01)

(52) U.S. Cl.
CPC ............ *A61F 2/447* (2013.01); *A61F 2/4425* (2013.01); *A61F 2002/443* (2013.01); *A61F 2310/00023* (2013.01); *A61F 2310/00317* (2013.01)

(58) Field of Classification Search
CPC .. A61F 2/447; A61F 2/4425; A61F 2002/443; A61F 2310/00023; A61F 2310/00317
USPC .......................................... 623/17.11–17.16
See application file for complete search history.

(56) References Cited

U.S. PATENT DOCUMENTS

| | | | | |
|---|---|---|---|---|
| 5,865,848 A * | 2/1999 | Baker | A61F 2/4455 | 606/279 |
| 7,799,081 B2 * | 9/2010 | McKinley | A61F 2/4611 | 623/17.16 |
| 8,062,375 B2 * | 11/2011 | Glerum | A61F 2/447 | 606/279 |
| 8,894,711 B2 * | 11/2014 | Varela | A61F 2/4611 | 623/17.16 |
| 9,034,041 B2 * | 5/2015 | Wolters | A61F 2/442 | 623/17.15 |
| 9,532,883 B2 * | 1/2017 | McLuen | A61F 2/28 | |
| 9,801,733 B2 * | 10/2017 | Wolters | A61F 2/447 | |
| 11,291,559 B1 * | 4/2022 | Yoon | A61F 2/4425 | |

(Continued)

OTHER PUBLICATIONS

Written Opinion mailed Jun. 24, 2022 in International Application No. PCT/US2022/017542.

(Continued)

*Primary Examiner* — Jessica Weiss
(74) *Attorney, Agent, or Firm* — Kim IP Law Group LLC

(57) ABSTRACT

An expandable intervertebral implant for an intervertebral fusion is provided. The implant includes a first endplate, a second endplate, a translation member and an auger mounted to the translation member and extending through the second endplate. The first endplate includes a sloped anterior face and a sloped posterior face. The second endplate includes a posteriorly facing sloped surface for matingly engaging the sloped anterior face of the first endplate. The translation member includes an anteriorly facing sloped surface for matingly engaging the sloped posterior face of the first endplate.

18 Claims, 26 Drawing Sheets

(56) References Cited

U.S. PATENT DOCUMENTS

| | | | | |
|---|---|---|---|---|
| 11,612,499 | B2 * | 3/2023 | Barfield | A61F 2/4455 623/17.16 |
| 2008/0147193 | A1 * | 6/2008 | Matthis | A61F 2/4465 623/17.16 |
| 2010/0191336 | A1 * | 7/2010 | Greenhalgh | A61F 2/4455 623/17.16 |
| 2011/0093074 | A1 * | 4/2011 | Glerum | A61F 2/447 623/17.16 |
| 2011/0282453 | A1 * | 11/2011 | Greenhalgh | A61F 2/4425 623/17.16 |
| 2012/0185049 | A1 * | 7/2012 | Varela | A61F 2/447 623/17.16 |
| 2012/0226357 | A1 * | 9/2012 | Varela | A61F 2/447 623/17.16 |
| 2012/0290090 | A1 * | 11/2012 | Glerum | A61F 2/447 623/17.16 |
| 2014/0236296 | A1 * | 8/2014 | Wagner | A61F 2/4455 623/17.15 |
| 2014/0243982 | A1 * | 8/2014 | Miller | A61F 2/447 623/17.16 |
| 2014/0249629 | A1 * | 9/2014 | Moskowitz | A61F 2/4611 623/17.15 |
| 2015/0182347 | A1 * | 7/2015 | Robinson | A61F 2/447 623/17.15 |
| 2015/0374509 | A1 * | 12/2015 | McLean | A61F 2/447 623/17.16 |
| 2016/0081814 | A1 * | 3/2016 | Baynham | A61F 2/447 623/17.16 |
| 2017/0367845 | A1 | 12/2017 | Eisen | |
| 2021/0137695 | A1 * | 5/2021 | Huang | A61F 2/4455 |

OTHER PUBLICATIONS

International Search Report mailed Jun. 24, 2022 in International Application No. PCT/US2022/017542.

Korean Intellectual Property Office, Office Action in counterpart Korean Patent Application No. 10-2022-7010411 issued Jan. 24, 2024.

Korean Intellectual Property Office, Office Action in counterpart Korean Patent Application No. 10-2022-7010411 issued Feb. 19, 2025.

* cited by examiner

EXPANDABLE INTERBODY FUSION DEVICE

CROSS-REFERENCE TO RELATED APPLICATION

This application is a continuation of U.S. patent application Ser. No. 17/194,034 filed on Mar. 5, 2021.

BACKGROUND OF THE INVENTION

The subject disclosure relates generally to an implant and method for promoting an intervertebral fusion. In particular, the subject disclosure relates to an expandable fusion device capable of being inserted between adjacent vertebrae to facilitate the fusion process.

A common procedure for handling pain associated with intravertebral discs that have become degenerated due to various factors such as trauma or aging is the use of intervertebral fusion devices for fusing one or more adjacent vertebral bodies. In order to use the adjacent vertebral bodies, the intervertebral disc must be partially or fully removed. An intervertebral fusion device is then inserted between neighboring vertebrae to maintain normal disc spacing and restore spinal stability, thereby providing an intervertebral fusion.

Conventional fusion devices include screw and rod arrangements, solid bone implants, and fusion devices which include a cage or other implant mechanism which, typically, is packed with bone and/or bone growth inducing substances. These devices are implanted between adjacent vertebral bodies in order to fuse the vertebral bodies together to alleviate associated pain.

However, there are drawbacks associated with conventional fusion devices. For example, typical expandable fusion cages are made of multiple components with many intricate mating features. Such components are made from subtractive manufacturing which can be time consuming to machine each component individually and consequently becomes expensive. Moreover, typical solid fusion cages do not provide anterior/posterior translation and may be undersized or oversized during implantation causing expulsion, creating a poor or delayed fusion result, and/or causing subsidence into an endplate of the vertebral body. As a result, inventories of different fixed cage heights are necessary. The above-mentioned factors result in higher market costs with slow turn around times and dead inventory.

Thus, there is still a need for a fusion device capable of being implanted that addresses the aforementioned problems of conventional fusion devices. Such a need is satisfied by the expandable intervertebral implant of the subject disclosure.

BRIEF SUMMARY

In accordance with an exemplary embodiment, the subject disclosure provides an expandable intervertebral implant having a first endplate, a second endplate, a translation member and an auger mounted to the translation member and extending through the second endplate. The first endplate includes a sloped anterior face and a sloped posterior face. The second endplate includes a posteriorly facing sloped surface for matingly engaging the sloped anterior face of the first endplate. The translation member includes an anteriorly facing sloped surface for matingly engaging the sloped posterior face of the first endplate.

In an aspect of the subject disclosure, the first endplate is movable relative to the second endplate between first and second positions. The second position is anteriorly spaced from the first position. The first endplate has a substantially trapezoidal-shaped side profile and further includes a superior facing central through hole. The sloped anterior face of the first endplate is angled relative to a longitudinal axis of the first endplate about 90-145 degrees. The auger is rotatably connected and/or secured to the translation member and extends through an anterior end of the second endplate. The auger is mounted within the translation member substantially flush with a bottom end of the translation member. At least one of the first endplate, second endplate, translation member and auger comprises silicon nitride.

In accordance with another aspect of the subject disclosure, the first endplate further includes an anterior female track and a posterior female track and the second endplate further includes a sloped male track for operatively engaging the anterior female track of the first endplate. The translation member includes a sloped female track for operatively engaging a posterior male tongue of the first endplate. The translation member is radiolucent. In accordance with yet another aspect of the subject disclosure, the translation member includes a through hole coaxial with a longitudinal axis of the auger when mounted to the translation member. The second endplate includes a retention track and the translation member includes a cooperating retention track for operatively engaging the retention track of the second endplate. The second endplate further includes a stop for operatively engaging the translation member at a predetermined position. At least one of the first and second endplates includes a variable density external surface or a variable textured teethed zone.

In accordance with yet another aspect of the subject disclosure, the first endplate includes a track about its midportion and the translation member includes a cooperating track about its anterior end engaging the first endplate track about its midportion. The sloped posterior face of the first endplate includes a radial protrusion for operatively engaging with a radial recess of the translation member when the translation member engages the first endplate. Additionally, the posteriorly facing sloped surface of the second endplate includes a first recess for facilitating angular expansion of the intervertebral implant. The anteriorly facing sloped surface of the translation member includes a second recess configured to receive a protrusion on the sloped posterior face of the first endplate.

The subject disclosure further provides a method of manufacturing an endplate implant of an expandable intervertebral implant comprising the step of using a computer aided design endplate model having a sloped anterior face, a sloped posterior face, and a superior face, wherein the sloped anterior face is angled greater than 10 degrees from the superior face, additively manufacturing the endplate implant based on the computer aided design endplate model with successive layers substantially parallel to the sloped anterior face. In an aspect of the subject disclosure, additively manufacturing the endplate implant utilizes silicon nitride, titanium, or combinations thereof.

In accordance with another exemplary embodiment, the subject disclosure provides an expandable intervertebral implant having a first endplate, a second endplate, a translation member and an auger mounted to the translation member and extending through the second endplate. The first endplate includes a sloped anterior face and a sloped posterior face having a radial protrusion. The second endplate includes a posteriorly facing sloped surface having a recess for matingly engaging the sloped anterior face of the first endplate. The translation member includes an anteriorly facing sloped surface having a radial recess, wherein the radial protrusion of the first endplate operatively engages the radial recess of the translation member when the translation member engages the first endplate. When the radial protrusion of the first endplate engages the radial recess of the translation member, the first endplate moves from a first position at a first angle relative to a longitudinal axis of the implant to a second position at a second angle relative to the longitudinal axis of the implant greater than the first angle.

In accordance with yet another exemplary embodiment, the subject disclosure provides an expandable intervertebral implant having a body and a cap. The body includes an upper surface, a lower surface, and a pair of side surfaces, wherein at least one of the upper surface, lower surface and side surfaces of the body includes a recess. The cap is configured to seat within the recess of the at least one of the upper surface, lower surface and side surfaces of the body. Additionally, the cap comprises at least one of a variable textured teethed zone, a variable density external surface, and a substantially smooth surface. In an aspect of the subject disclosure, the cap comprises silicon nitride, titanium or combinations thereof. The expandable intervertebral implant further includes a second cap configured to seat in a second recess of at least one of the upper surface, lower surface and side surfaces of the body.

BRIEF DESCRIPTION OF THE SEVERAL VIEWS OF THE DRAWINGS

The foregoing summary, as well as the following detailed description of the exemplary embodiments of the subject disclosure, will be better understood when read in conjunction with the appended drawings. For the purpose of illustrating the subject disclosure, there are shown in the drawings exemplary embodiments. It should be understood, however, that the exemplary embodiments of the subject disclosure are not limited to the precise arrangements and instrumentalities shown.

In the drawings.

DETAILED DESCRIPTION OF THE INVENTION

Figure 1:
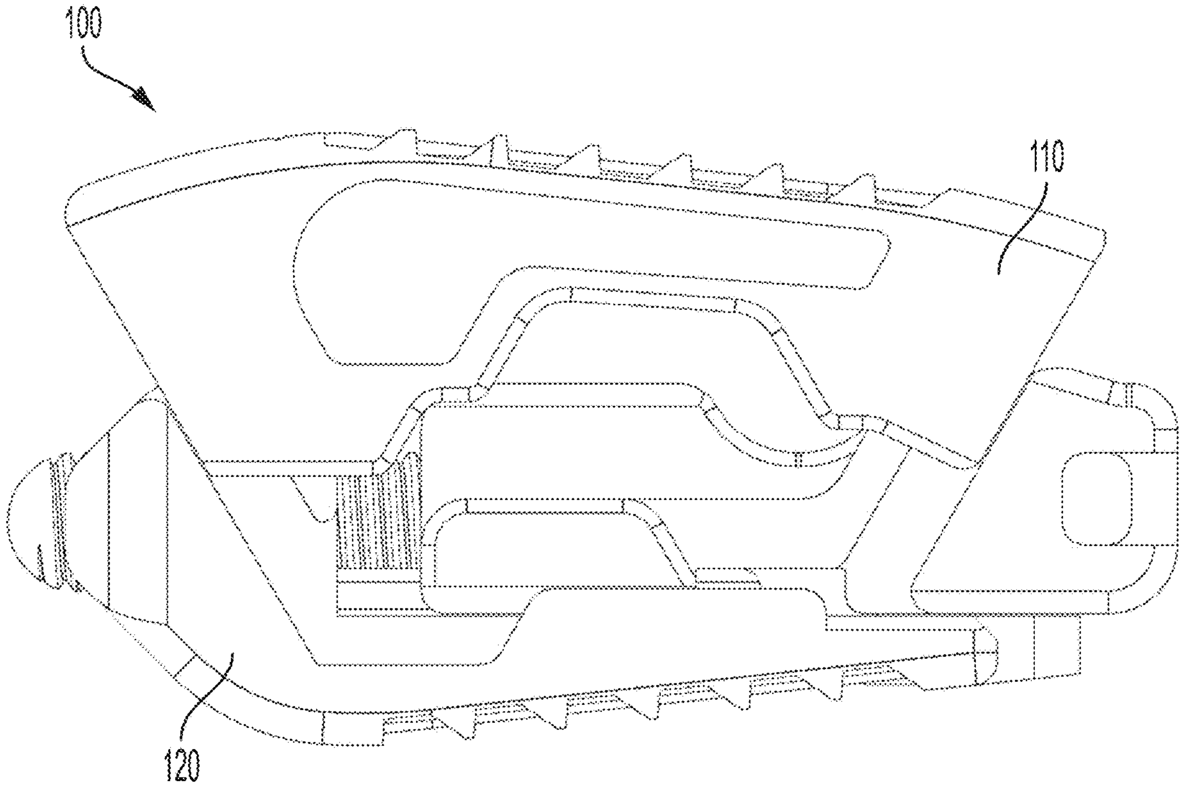
FIG. 1 is a side view of an expandable intervertebral implant in accordance with an exemplary embodiment of the subject disclosure in an expanded position.

Reference will now be made in detail to the exemplary embodiments of the subject disclosure illustrated in the accompanying drawings. Wherever possible, the same or like reference numbers will be used throughout the drawings to refer to the same or like features. It should be noted that the drawings are in simplified form and are not drawn to precise scale. Certain terminology is used in the following description for convenience only and is not limiting. Directional terms such as top, bottom, left, right, above, below and diagonal, are used with respect to the accompanying drawings. The term "distal" shall mean away from the center of a body. The term "proximal" shall mean closer towards the center of a body and/or away from the "distal" end. The words "inwardly" and "outwardly" refer to directions toward and away from, respectively, the geometric center of the identified element and designated parts thereof. Such directional terms used in conjunction with the following description of the drawings should not be construed to limit the scope of the subject disclosure in any manner not explicitly set forth. Additionally, the term "a," as used in the specification, means "at least one." The terminology includes the words above specifically mentioned, derivatives thereof, and words of similar import.

"About" as used herein when referring to a measurable value such as an amount, a temporal duration, and the like, is meant to encompass variations of ±20%, ±10%, ±5%, ±1%, or ±0.1% from the specified value, as such variations are appropriate.

"Substantially" as used herein shall mean considerable in extent, largely but not wholly that which is specified, or an appropriate variation therefrom as is acceptable within the field of art. "Exemplary" as used herein shall mean serving as an example.

Throughout this disclosure, various aspects of the exemplary embodiments can be presented in a range format. It should be understood that the description in range format is merely for convenience and brevity and should not be construed as an inflexible limitation on the scope of the exemplary embodiments. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Furthermore, the described features, advantages and characteristics of the exemplary embodiments may be combined in any suitable manner in one or more embodiments. One skilled in the relevant art will recognize, in light of the description herein, that the exemplary embodiments can be practiced without one or more of the specific features or advantages of a particular embodiment. In other instances, additional features and advantages may be recognized in certain embodiments that may not be present in all embodiments of the subject disclosure.

Figure 1A:
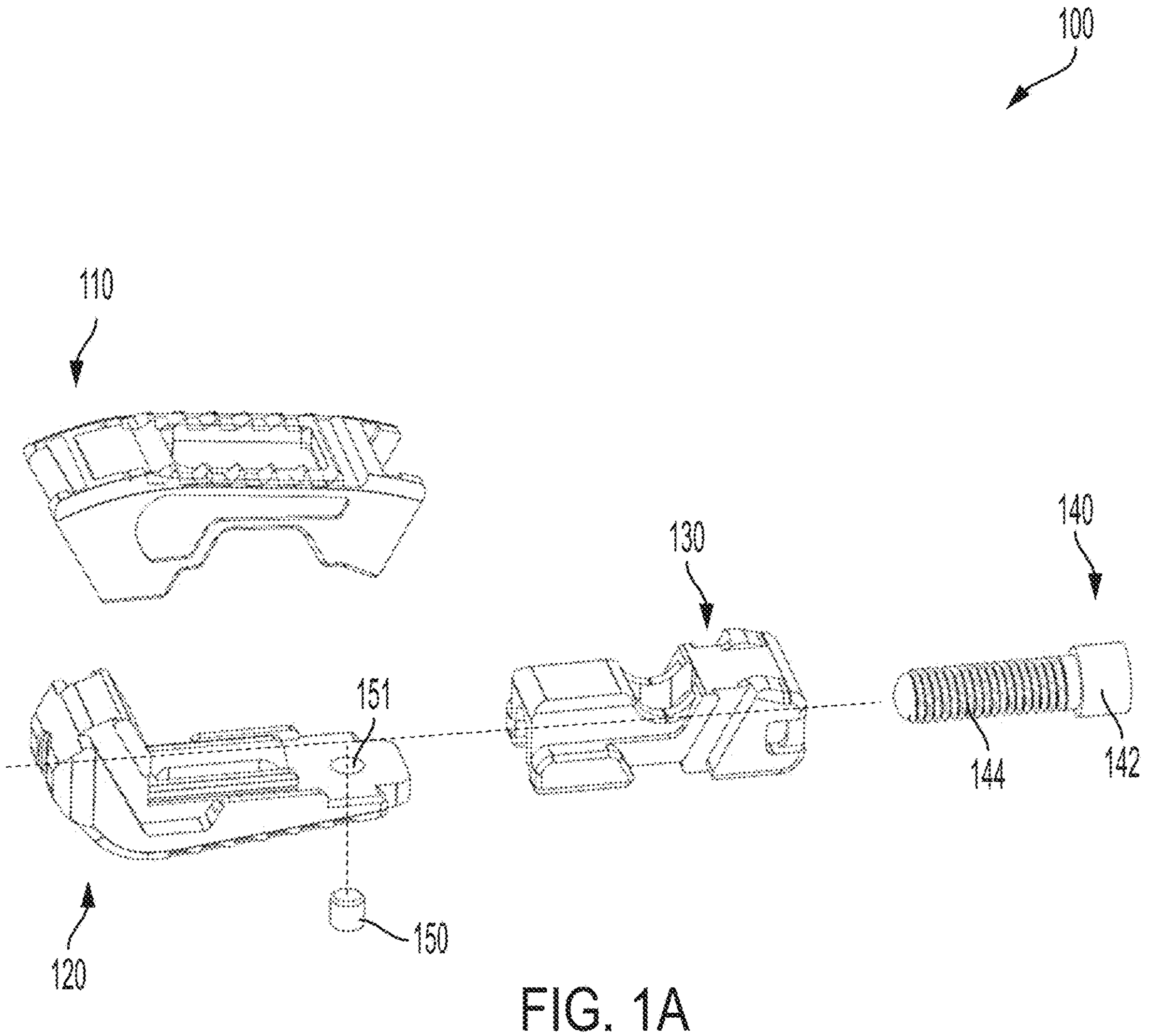
FIG. 1A is an exploded, perspective view of the expandable intervertebral implant of FIG. 1.
Figure 2:
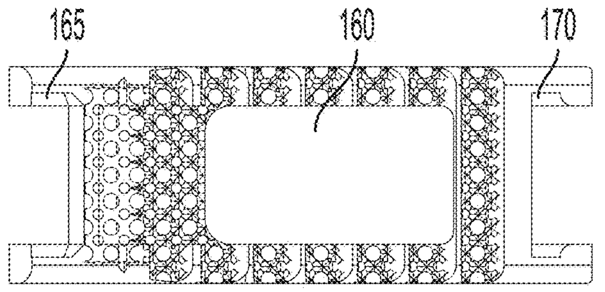
FIG. 2 is a top view of a first endplate of the expandable intervertebral implant of FIG. 1.

Referring to FIGS. 1, 1A and 21-29, there is shown an exemplary embodiment of an expandable intervertebral implant 100 in accordance with the subject disclosure. As shown in FIG. 1A, the intervertebral implant 100 includes a first endplate 110, a second endplate 120, a translation member 130 and an auger 140 mounted to the translation member 130. In general, the first endplate 110 and second endplate 120 are configured to engage the translation member 130.

The expandable intervertebral implant 100 can be manufactured from a number of materials including titanium, stainless steel, titanium alloys, non-titanium metallic alloys, polymeric materials, e.g., plastics, plastic composites, polyetheretherketone (PEEK), and ceramics such as silicon nitride ($Si_3N_4$), zirconium oxide ($ZrO_2$), silver oxide ($Ag_2O$), and other suitable materials, both radiopaque and radiolucent.

Advantageously, ceramics such as silicon nitride produce alkaline compounds that are lethal to bacteria and promote osteo-integration. See Pezzotti, G. et al. Silicon Nitride Bioceramics Induce Chemically Driven Lysis in *Porphyromonas gingivalis. Langmuir* 32, 3024-3035 (2016) and Webster, T J et al. "Anti-infective and osteointegration properties of silicon nitride, poly(ether ether ketone), and titanium implants." *Acta biomaterialia* vol. 8, 12 (2012): 4447-54. Additionally, silicon nitride has osteoinductive, osteoconductive, and/or germicidal surface properties that promote bone formation and tissue development. Silicon nitride is also inherently resistant to bacteria and biofilm formation. See e.g., Ishikawa, Masahiro et al. "Surface topography of silicon nitride affects antimicrobial and osseointegrative properties of tibial implants in a murine model." *Journal of biomedical materials research*. Part A vol. 105, 12 (2017): 3413-3421. doi:10.1002/jbm.a.36189.

As oriented in FIGS. 1-9, the first endplate 110 is the top, superior and/or upper endplate and the second endplate 120 is the bottom, inferior and/or lower endplate. As described below, the first endplate 110 and second endplate 120 may include similar features and a discussion of such features will be applicable to both first and second endplates, unless stated otherwise.

As shown in FIGS. 1-5, the first endplate 110 includes a sloped anterior face 111 and a sloped posterior face 112. The sloped anterior face 111 is angled (a) relative to a longitudinal axis (A) of the first endplate about 90-145 degrees, including 95, 100, 105, 110, 115, 120, 125, 130, 135, and 140 degrees. The first endplate further includes an upper surface 113, a lower surface 114 and a central through hole 160. The through hole 160 passes from the upper surface 113 to the lower surface 114. The through hole 160, in an exemplary embodiment, is sized to receive bone graft or similar bone growth inducing material to be packed in a center of the implant 100. In other words, the through hole 160 can be configured to enable bone graft material deposited within the implant 100 to engage, contact and/or fuse with an adjacent vertebral body. The upper surface 113 may be referred to as an outer surface and/or a superior surface. Similarly, the lower surface 114 may be referred to as a bottom surface and/or an inferior surface.

Figure 3:
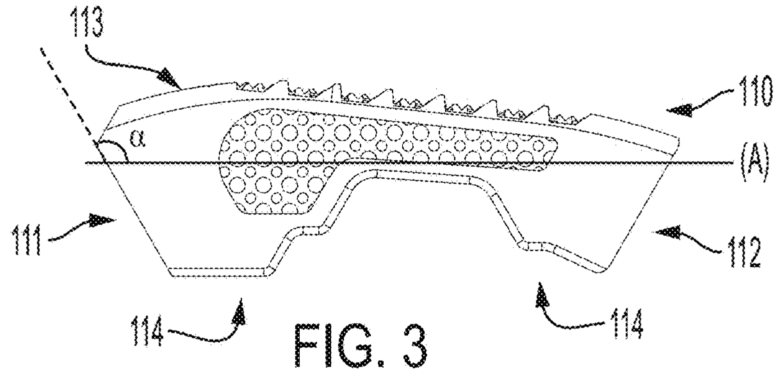
FIG. 3 is a side view of the first endplate of the expandable intervertebral implant of FIG. 1.
Figure 4:
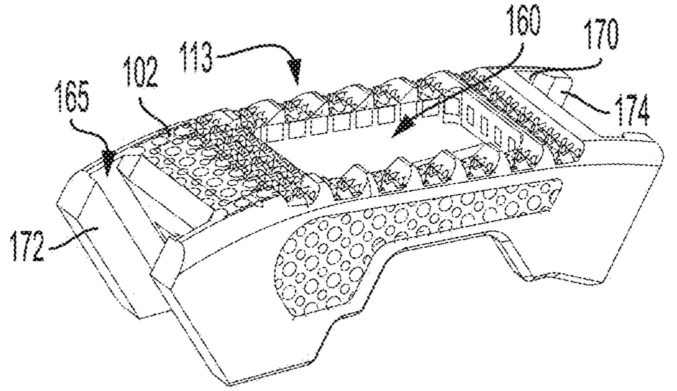
FIG. 4 is a perspective view of the first endplate of the expandable intervertebral implant of FIG. 1.

As shown in FIGS. 3 and 4, the upper surface 113 of the first endplate 110 is generally planar to allow the upper surface 113 of the first endplate 110 to engage with adjacent vertebral bodies. However, the upper surface 113 can be curved more convexly or concavely to allow for a greater or lesser degree of engagement with adjacent vertebral bodies. It is also contemplated that the upper surface 113 can be generally planar but include a generally straight ramped surface or a curved ramp surface to allow for engagement with adjacent vertebral bodies in a lordotic fashion.

In an exemplary aspect, the first endplate 110 is configured having a substantially trapezoidal-shaped side profile, as best shown in FIG. 3. However, the side profile of the first endplate 110 can be configured as any shape suitable for the foregoing intended use and/or design criteria, e.g., rectangular, triangular and the like.

Figure 30:
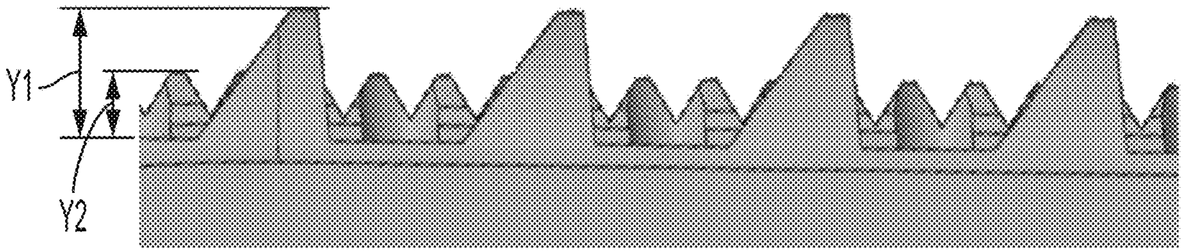
FIG. 30 is an isolated side view of a variable density external surface of the expandable intervertebral implant of FIG. 1.
Figure 31:
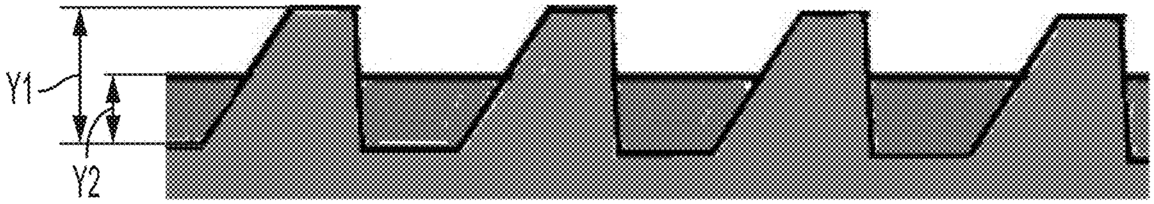
FIG. 31 is an isolated side view of a variable textured teethed zone of the expandable intervertebral implant of FIG. 1.
Figure 32:
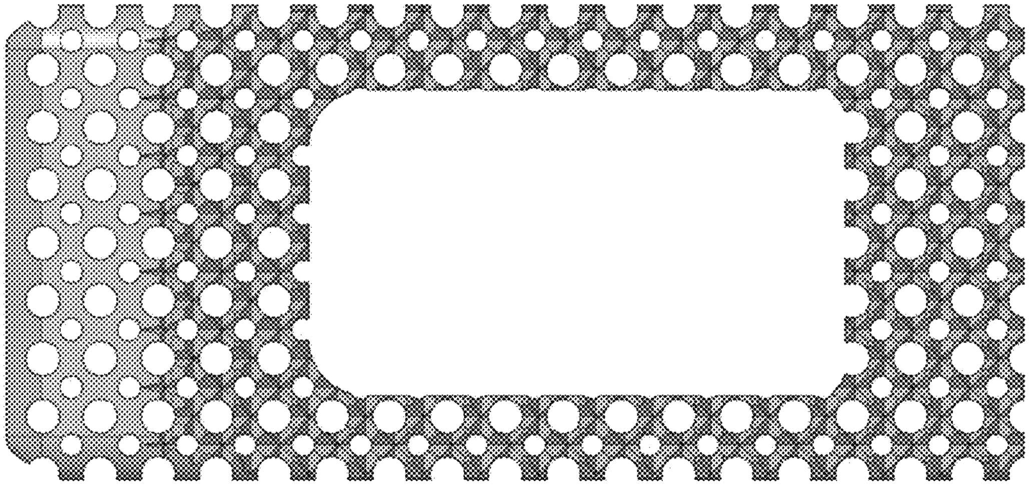
FIG. 32 is an isolated top view of a textured surface of the expandable intervertebral implant of FIG. 1.

In an aspect of the exemplary embodiment, the upper surface 113 includes texturing 102 to aid in gripping adjacent vertebral bodies. As shown in FIGS. 2-5 and FIGS. 30-32, the texturing 102 can be a variable density external surface (FIG. 30) or a variable textured teethed zone (FIG. 31). The variable density external surface can be manufactured using a topology optimization method and/or algorithm to create a lightweight intervertebral implant having a desired variable feel or firmness and/or shape retention in one region of the implant relative to another region of the implant. Such topology optimization can be utilized to customize implants based on the needs of a particular patient. The texturing can include, but is not limited to, teeth, ridges, friction increasing elements, patterned divots, through holes, keels or gripping or purchasing projections. In accordance with an aspect, side surfaces adjacent the upper surface 113 and lower surface 114 include similar texturing including, but not limited to, teeth, ridges, friction increasing elements, patterned divots, through holes, keels or gripping or purchasing projections. As shown in FIGS. 30 and 31, the texturing can be a multi-density and/or variable textured teethed zone having a height Y1 with a trabecular zone having a height Y2.

The variable density external surface is achieved by controlling the volume to porosity ratio of the subject external surface. For example, the malleability/deformability of the surface can be achieved by decreasing the volumetric density (i.e., increasing porosity) and by decreasing the thickness of the external surface layer. This can be accomplished through various techniques including, but not limited to, additive manufacturing, subtractive manufacturing, chemical subtraction, laser texturing, and the like.

Referring back to FIGS. 4 and 5, the first endplate 110 further includes one or more mating elements, e.g., an anterior female track 165 and posterior female track 170. The anterior female track 165 and posterior female track 170 can be, for example, configured as a recess (e.g., a groove, track and/or channel). As shown in FIG. 4, the anterior female track includes an anterior male tongue 172 and the posterior female track includes a posterior male tongue 174. The anterior male tongue 172 forms part of the anterior female track 165 and the posterior male tongue 174 forms part of the posterior female track 170. The anterior female track 165 and posterior female track 170 operatively engage with complementary or corresponding mating elements on the second endplate 120 and the translation member 130 to form a slidable joint. That is, the second endplate 120 and the translation member 130 are configured to slideably engage the first endplate 110. The slideable joint advantageously enables the implant 100 to transition between an expanded and collapsed position, as well as expansion in the anterior posterior direction. That is, the implant can expand in both height and in the anterior posterior direction e.g., between first and second height positions and between first and second anterior posterior positions.

As shown in FIGS. 1A and 6-9, the second endplate 120 includes a posteriorly facing sloped surface 122 for matingly engaging the sloped anterior face 111 of the first endplate 110. The second endplate 120 further includes an upper surface 124, a lower surface 126, an anterior end 127 and posterior end 128. Similar to the first endplate 110, the second endplate 120 includes a central through hole 125. The through hole 125 passes from the upper surface 124 to the lower surface 126. The through hole 125, in an exemplary embodiment, is sized to receive bone graft or similar bone growth including material to be packed in a center of the implant 100. In other words, the through hole 125 can be configured to enable bone graft material deposited within the implant 100 to engage, contact and/or fuse with an adjacent vertebral body.

In an aspect of the exemplary embodiment, the lower surface 126 of the second endplate 120 includes texturing

104 to aid in gripping the adjacent vertebral bodies. The texturing can be the same texturing as described above for the first endplate. That is, similar to the texturing of the first endplate 110, the texturing 104 can be a variable density external surface or a variable textured teethed zone.

Figure 8:
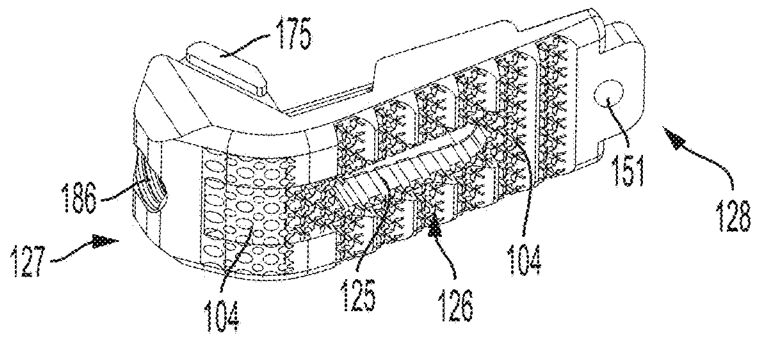
FIG. 8 is a bottom perspective view of the second endplate of the expandable intervertebral implant of FIG. 1.
Figure 9:
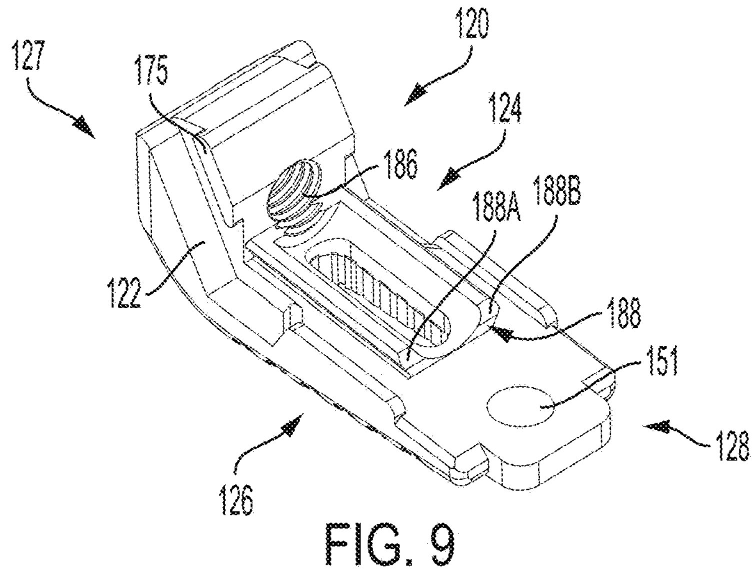
FIG. 9 is another perspective view of the second endplate of the expandable intervertebral implant of FIG. 1.
Figure 10:
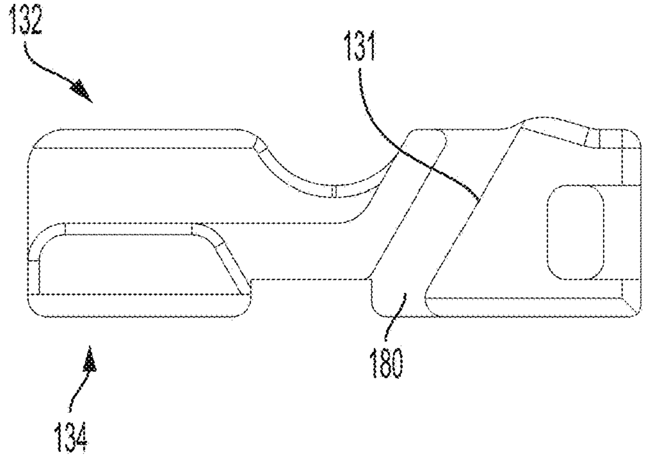
FIG. 10 is a side view of a translation member of the expandable intervertebral implant of FIG. 1.
Figure 11:
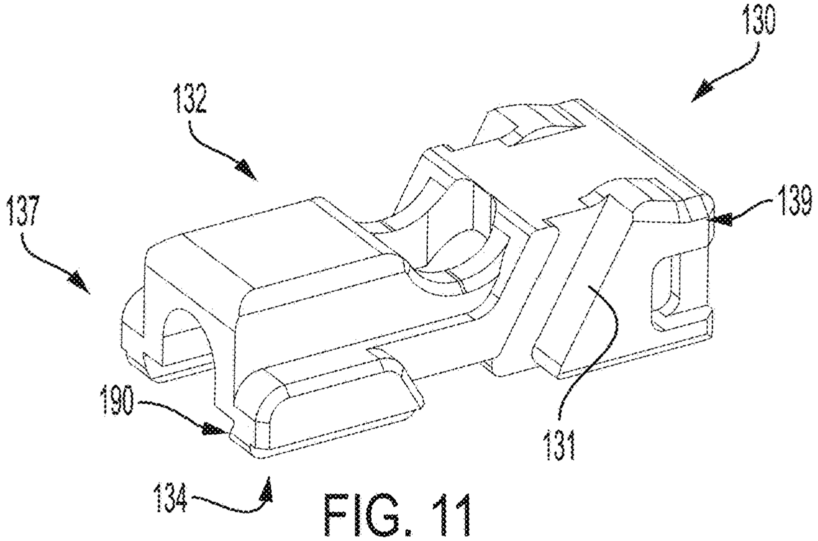
FIG. 11 is a perspective view of the translation member of the expandable intervertebral implant of FIG. 1.
Figure 12:
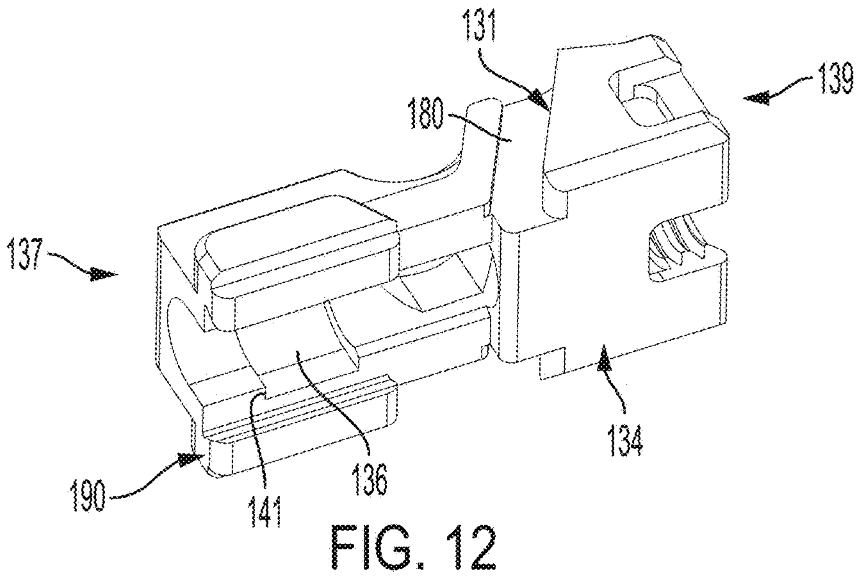
FIG. 12 is a bottom perspective view of the translation member of the expandable intervertebral implant of FIG. 1.
Figure 13:
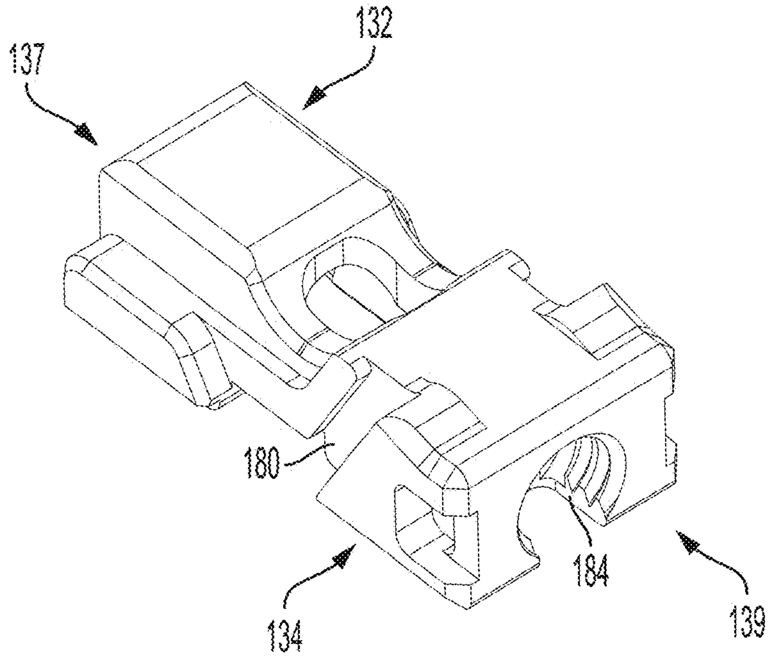
FIG. 13 is another perspective view of the translation member of the expandable intervertebral implant of FIG. 1.

As shown in FIGS. 8-9, the second endplate includes a through hole 186 about its anterior end 127 for receiving the auger 140 therethrough. The through hole 186 is an anterior facing through hole and is located about the anterior end 127 of the second endplate 120. The through hole 186 contains threads along its inner surface for engaging the auger 140. A longitudinal axis of the through hole 186 extends in the same direction as a longitudinal axis of the second endplate.

Referring to FIGS. 8-9, the second endplate 120 further includes a sloped male track 175 for operatively engaging the anterior female track 165 of the first endplate 110. The sloped male track 175 is configured as shown in FIG. 8 e.g., as a tongue. However, it can be configured as any other suitable element including, but not limited to, a ridge, tooth or projection. When assembled, the sloped male track 175 slidingly engages the anterior female track 165 of the first endplate 110.

The second endplate 120 further includes a retention track 188 about its upper surface 124 for operatively engaging the translation member 130. The retention track 188 is configured as a longitudinally extending central dove-tail like track having a pair of lateral protrusions or shoulders 188A, 188B. The retention track 188 slideably engages one or more cooperating tracks on the translation member 130, such as cooperating dove-tail like track 190. That is, when the second endplate 120 and translation member 130 are assembled together, the retention track 188 forms a slidable joint with a corresponding mating element 190 on the translation member 130, as further discussed below.

As shown in FIG. 9, the retention track 188 extends longitudinally about the center of the second endplate 120 and is positioned posteriorly to the through hole 186. The retention track 188 is also spaced from the posterior end 128 of the second endplate 120.

Preferably, at least one of the first endplate 110 and second endplate 120 comprises silicon nitride. Additionally, both the first and second endplates can comprise silicon nitride, partially or fully. The first endplate and second endplate can also include other ceramics such as zirconium oxide ($ZrO_2$), silver oxide ($Ag_2O$), and other suitable materials, both radiopaque and radiolucent. As previously discussed above, at least one of the first endplate 110 and second endplate 120 includes a variable density external surface. Similarly, at least one of the first endplate 110 and second endplate 120 includes a variable textured teethed zone. That is, both the first and second endplates can comprise a combination of variable density external surfaces and variable textured teethed zones.

As shown in FIGS. 1A and 10-13, the translation member 130 includes one or more mating elements configured to mate with complementary mating elements on the first endplate 110. Specifically, the translation member 130 includes an anteriorly facing sloped surface 131 for matingly engaging the sloped posterior face 112 of the first endplate 110. The translation member 130 further includes a sloped female track 180 for operatively engaging the posterior male tongue 174 of the first endplate 110.

For purposes of clarity and reference, the translation member 130 includes an upper surface 132, lower surface 134, an anterior end 137 and a posterior end 139. As discussed above, the translation member 130 includes a cooperating retention track 190 for operatively engaging the retention track 188 of the second endplate 120. The cooperating retention track 190 is configured as a recess (e.g., a groove, track, cooperating dove-tail like track, and/or channel) for receiving the retention track 188.

In general, both the sloped female track 180 and cooperating retention track 190 allow the translation member 130 to operatively engage the second endplate 120 and translate laterally along a longitudinal direction of the second endplate and operatively engage the first endplate 110 to translate the first endplate upwardly or downwardly.

The translation member 130 includes a through hole 184 about its posterior end 139 that is coaxial with a longitudinal axis of the auger 140 when the auger 140 is mounted to the translation member 130. The through hole 184 can be a threaded through hole. The lower surface 134 of the translation member 130 also includes a recess 136 for mountably receiving and retaining the auger 140. The recess 136 includes a flange 141 at its anterior end which serves as a stop or limit for limiting travel of the auger therein.

In an aspect of the exemplary embodiment, the translation member 130 can be formed from a radiolucent material such that the spacing between the first and second endplates can be visible on radiographs, as well as the position of the auger 140. Alternatively, in another aspect, the translation member 130 can be formed from a radiopaque or semi-radiolucent material. In yet another aspect, the translation member 130 can be formed from materials that contain osteoinductive, osteoconductive, and/or germicidal surface properties (e.g., silicon nitride, zirconium oxide, or silver oxide) for promoting bone formation and tissue development within the implant.

Using a material that contains osteoinductive and osteoconductive properties is particularly advantageous because there is a gap between the first endplate 110 and the second endplate 120 when the intervertebral implant 100 is assembled. That is, when the intervertebral implant 100 is in an expanded configuration (FIGS. 25, 28 and 29) or a collapsed configuration (FIGS. 24, 26 and 27), the translation member 130 is positioned between the first endplate and second endplate. Thus, with a translation member made of silicon nitride, the translation member will promote bone growth and tissue development within the gap owing to the silicon nitride material. The osteoinductive and osteoconductive properties of silicon nitride results in accelerated bone healing, bone fusion and implant integration with the surrounding bone.

Figure 4A:
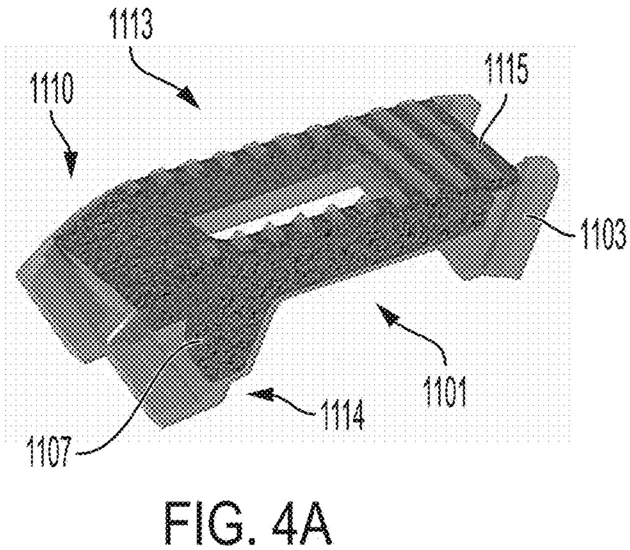
FIG. 4A is a perspective view of the first endplate of the expandable intervertebral implant of FIG. 1.
Figure 4B:
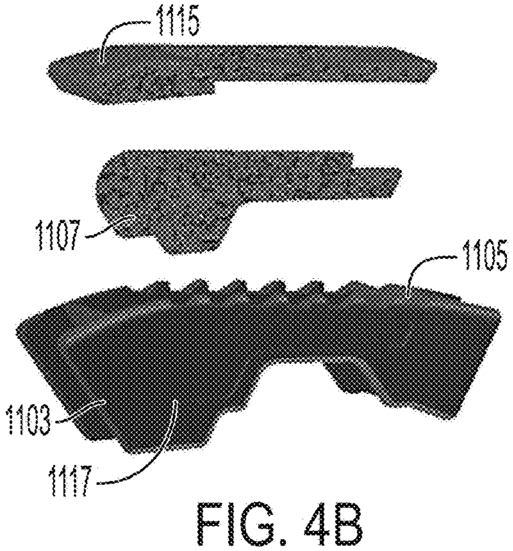
FIG. 4B is an exploded perspective view of the first endplate of FIG. 4A.
Figure 5:
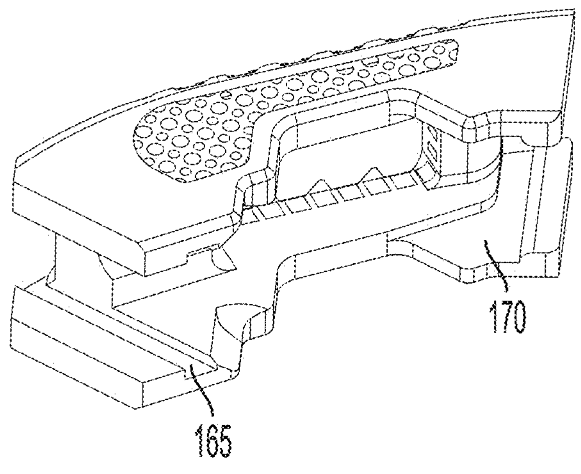
FIG. 5 is a bottom perspective view of the first endplate of the expandable intervertebral implant of FIG. 1.
Figure 6:
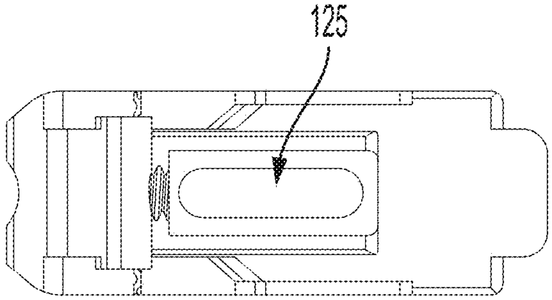
FIG. 6 is a top view of a second endplate of the expandable intervertebral implant of FIG. 1.
Figure 7:
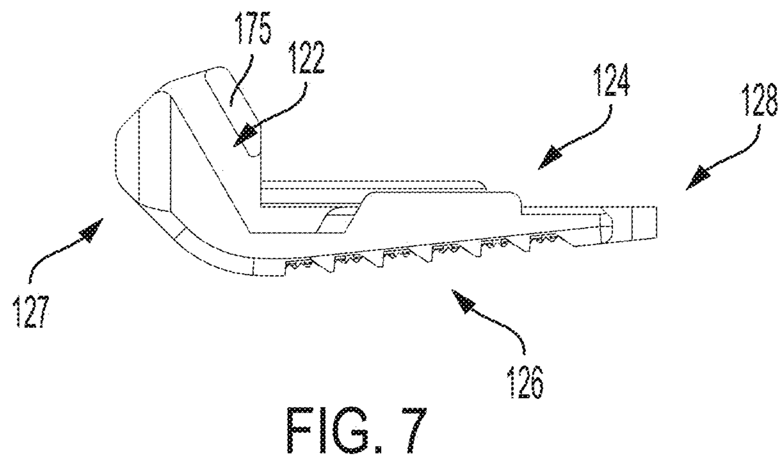
FIG. 7 is a side view of the second endplate of the expandable intervertebral implant of FIG. 1.

FIGS. 4A-4B and 8A-8B illustrate an alternative exemplary embodiment of a first and second end plate 1110 and 1120, respectively. The first endplate 1110 of the expandable intervertebral implant includes a body having an upper surface 1113, a lower surface 1114, and a pair of side surfaces 1101. The first endplate 1110 is similarly configured to the first endplate 110 (FIG. 4) except that the texturing is provided on a removable cap. In other words, as shown in FIGS. 4A-4B, at least one of the upper surface 1113, lower surface 1114, or side surfaces 1101 of the body 1110 includes a recess or at least one recess for receiving a cap containing texturing that corresponds to the size and shape of the recess. The removable cap is complementary shaped to the recess to matingly be received therein.

The upper surface can include a recess 1105 for receiving a removable cap 1115, which is complementary shaped. The side surface can include a recess 1117 for receiving a removable cap 1107, which is complementary shaped. The respective caps 1107, 1115 have texturing similar to texturing 102 on the first endplate 110. It is to be understood that the texturing on both the upper surface 1113 and side surfaces 1101 can be completely or partially provided by the cap 1107, 1115. Similar to the texturing 102 on the upper surface 113 of the first endplate 110, each cap 1107, 1115 can be formed to have a variable density or a variable textured teethed zone. Each cap 1107, 1115 can include, but is not limited to, texturing that includes teeth, ridges, friction increasing elements, knurlings, patterned divots, through holes, keels or gripping or purchasing projections. The cap 1107 can include a lip (not shown) to facilitate securing the cap 1107 to the recess 1117. As shown in FIGS. 4A-4B, the cap 1107, 1115 is positioned adjacent a solid zone 1103 of the first endplate 1110.

Figure 8A:
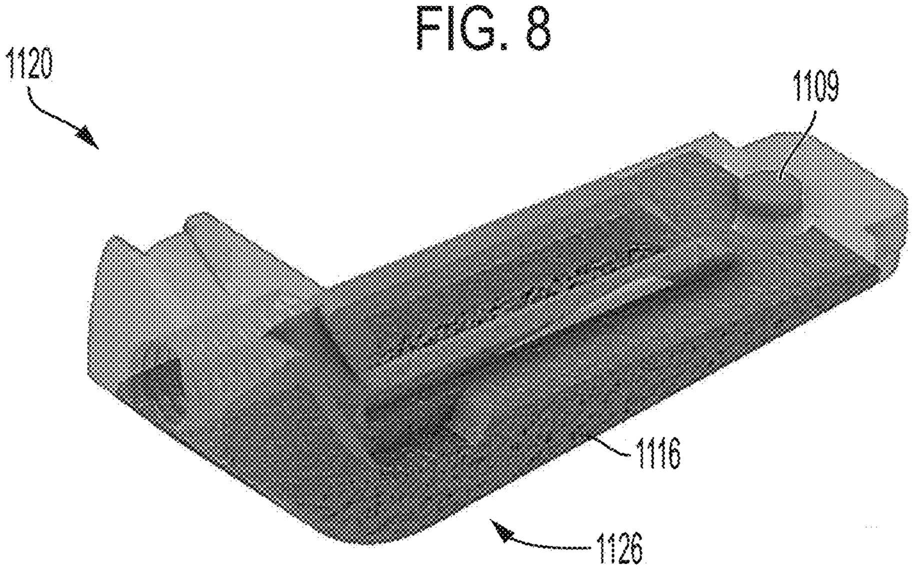
FIG. 8A is another perspective view of the second endplate of the expandable intervertebral implant of FIG. 1.
Figure 8B:
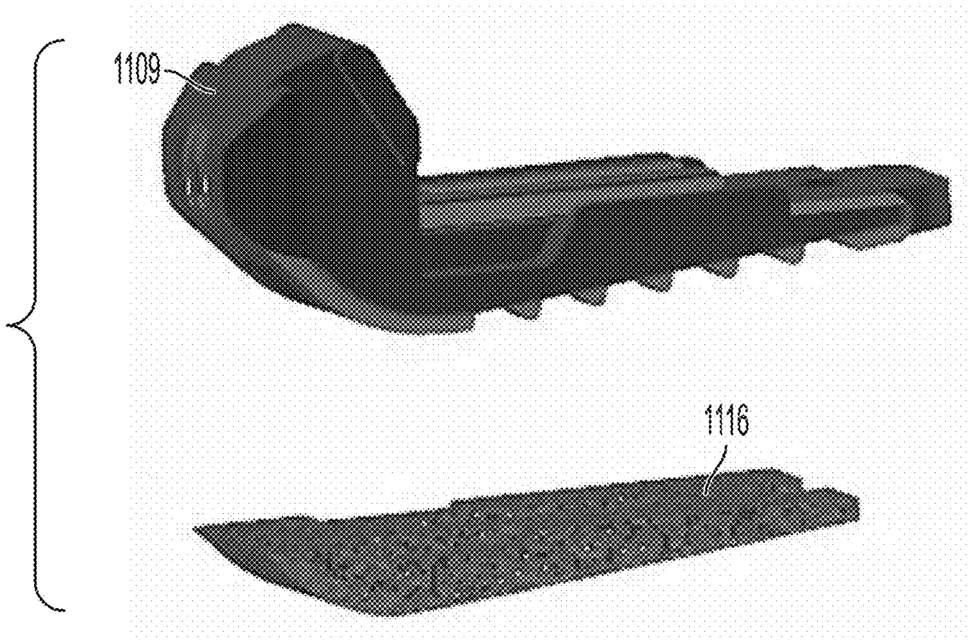
FIG. 8B is an exploded perspective view of the second endplate of FIG. 8A.

Referring now to FIGS. 8A-8B, similar to the first endplate 1110 discussed above, a lower surface 1126 of the second endplate 1120 can also include a removable cap 1116 having texturing similar to the texturing on each cap 1107, 1115 of the first endplate 1110. It is to be understood that the cap 1116 can be received within a complementary shaped recess (not shown) on the lower surface 1126 of the second endplate 1120. As shown in FIGS. 8A-8B, the cap 1116 is positioned adjacent a solid zone 1109 of the second endplate 1120.

Figure 42:
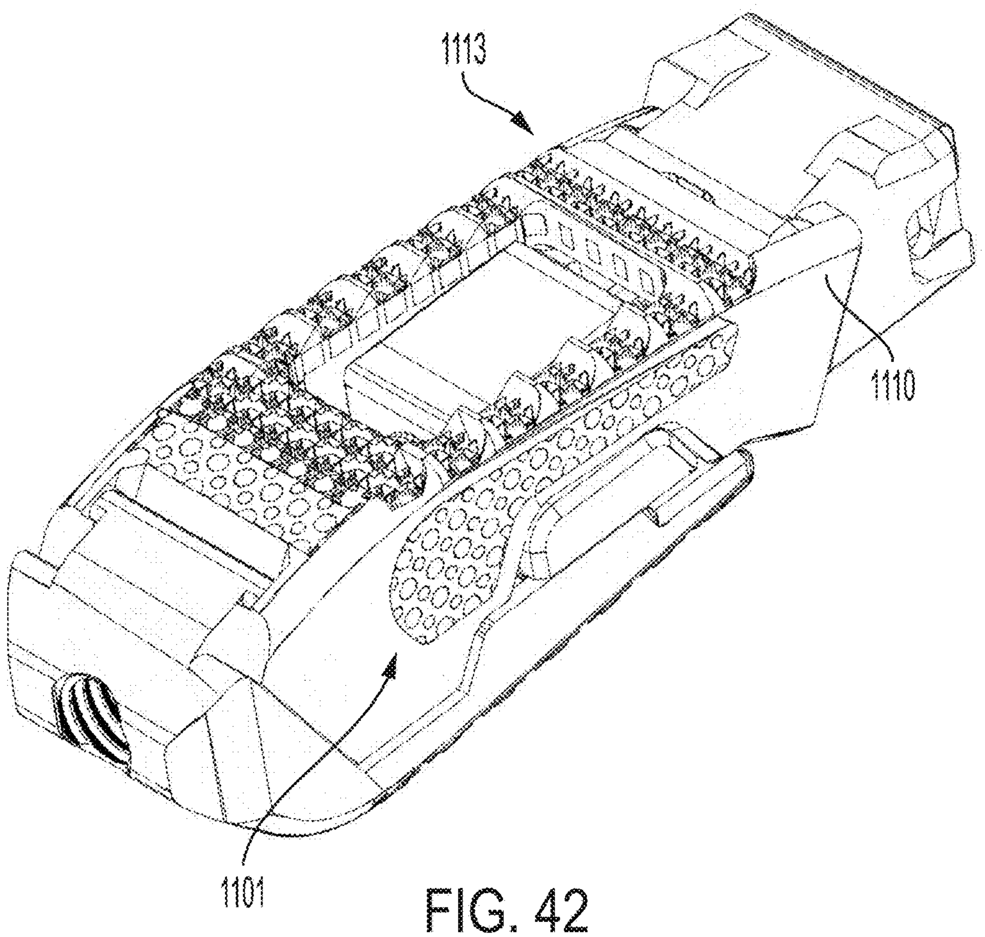
FIG. 42 is a perspective view of the fully assembled expandable intervertebral implant of FIG. 1 with a plurality of textured surfaces.
Figure 43:
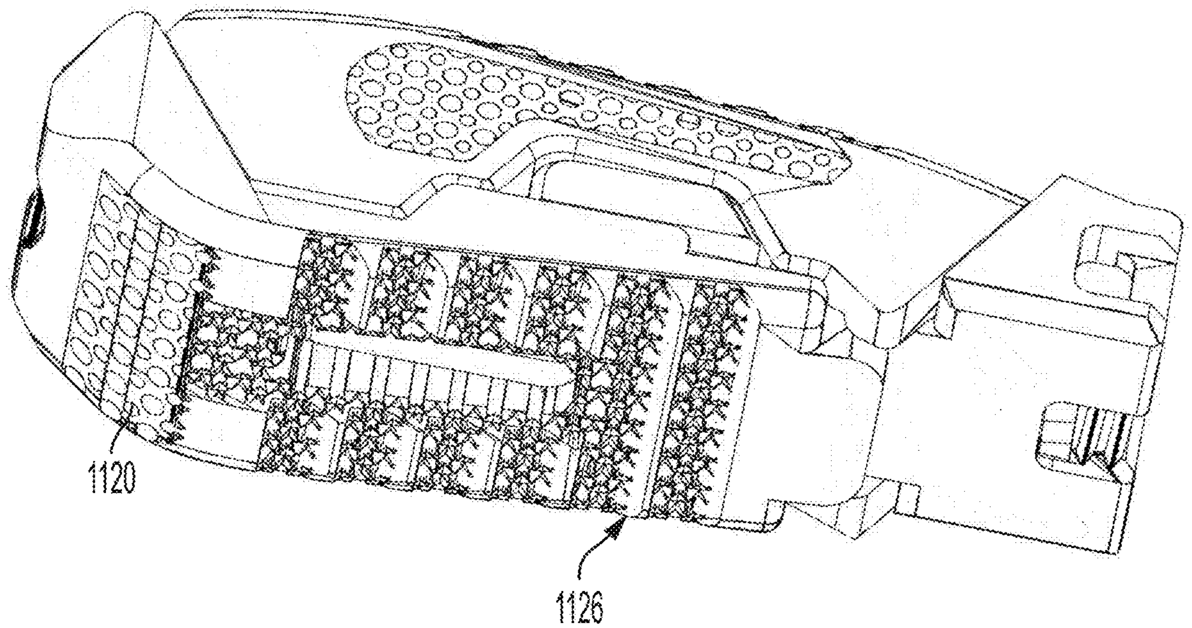
FIG. 43 is another perspective view of the fully assembled expandable intervertebral implant of FIG. 1 with a textured surface.
Figure 44:
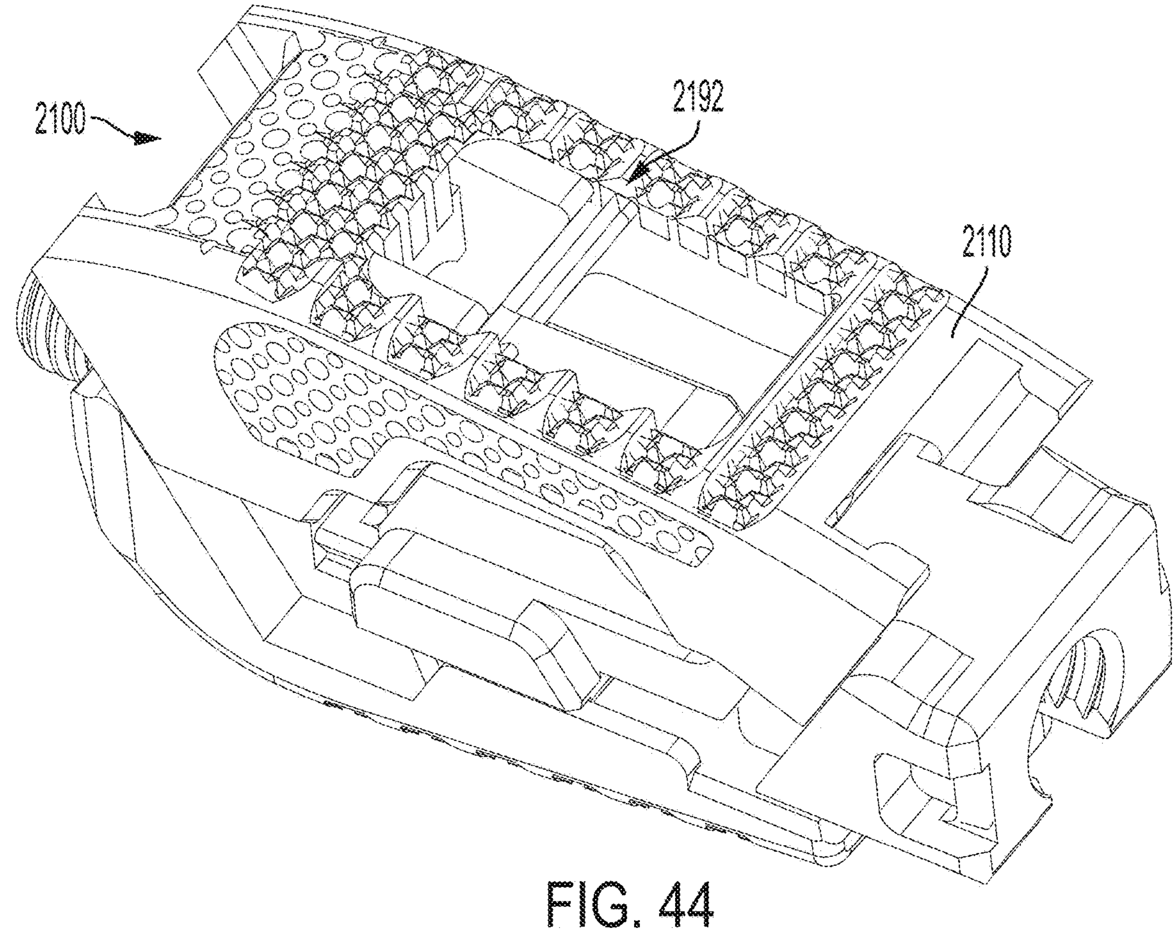
FIG. 44 is a perspective view of an expandable intervertebral implant in accordance with another exemplary embodiment of the subject disclosure.
Figure 45:
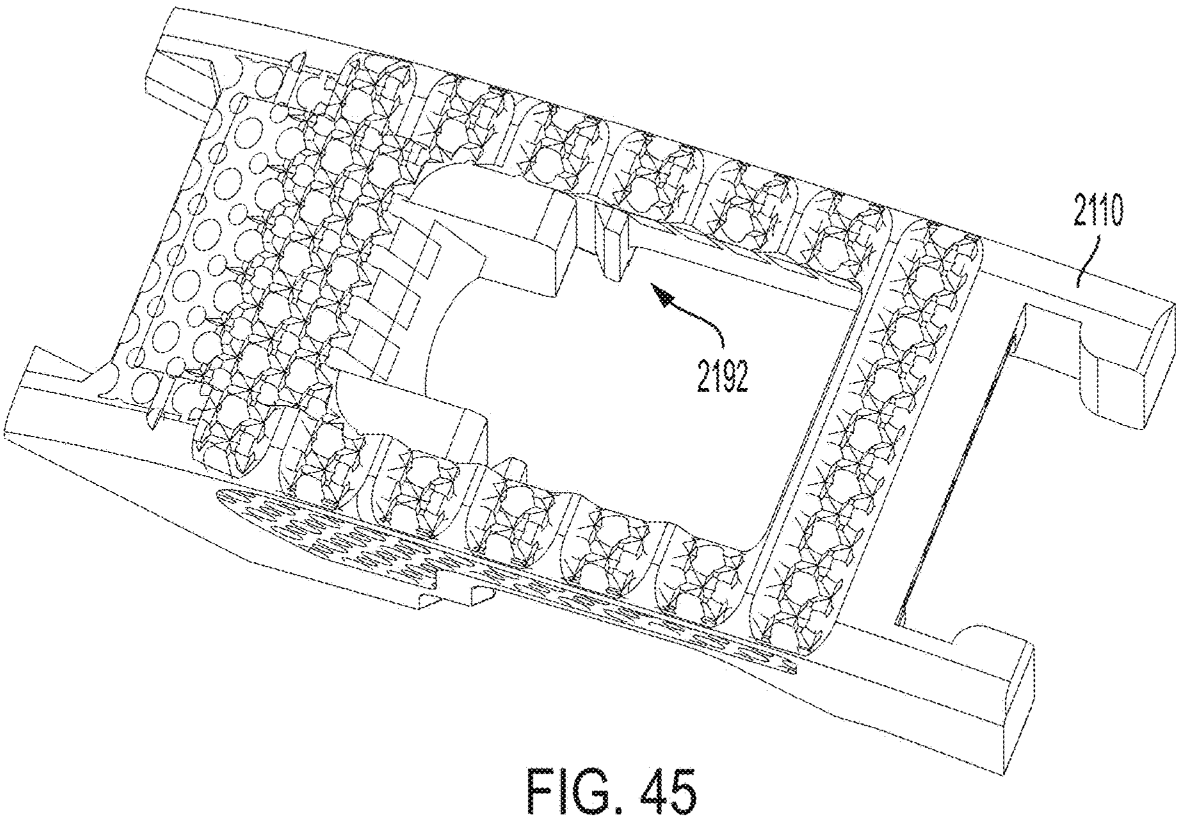
FIG. 45 is a top perspective view of a first endplate of the expandable intervertebral implant of FIG. 44.
Figure 46:
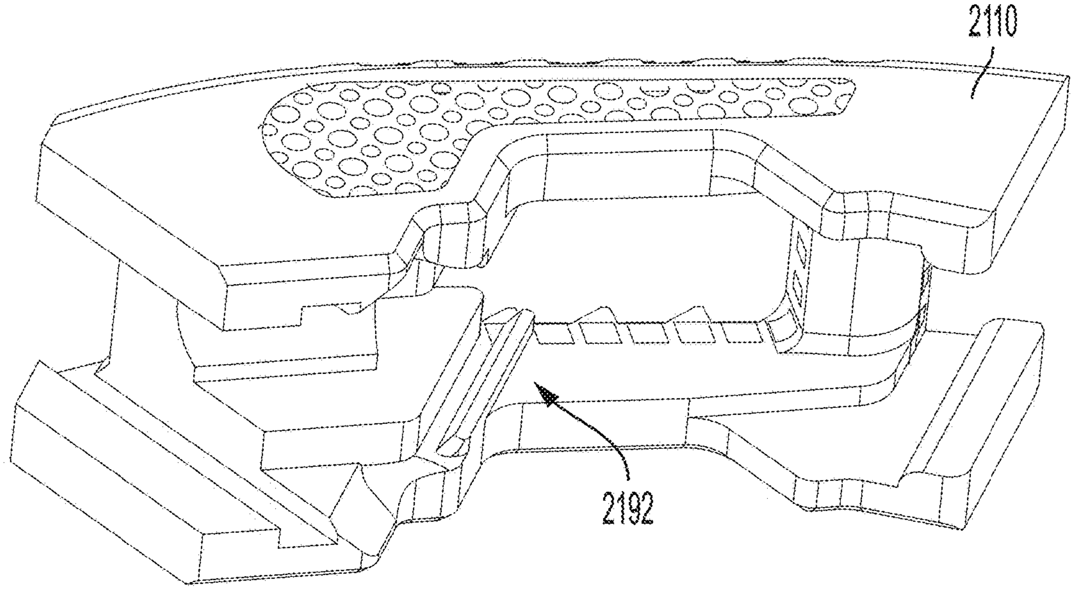
FIG. 46 is a bottom perspective view of the first endplate of the expandable intervertebral implant of FIG. 44.

In accordance with an aspect as shown in FIGS. 4A-4B and 8A-8B, caps 1107, 1115, 1116 can be releasably mounted in the respective recesses on the first endplate and second endplate. Alternatively, the cap 1107, 1115, 1116 can be integrally formed with the respective surfaces of the first endplate and second endplate. In general, as shown in FIGS. 42-43, the texturing can be a variable density external layer or a variable textured teethed zone on the upper surface 1113 of the first endplate 1110, the side surfaces 1101 of the first endplate 1110, or the lower surface 1126 of the second endplate 1120. It is to be understood that a standalone cap containing texturing can be releasably mounted to other applicable intervertebral implants and/or secondary cages, such as those shown in FIGS. 53A-E.

During assembly, the cap 1107, 1115, 1116 may be press fit, adhesively attached, fastened by a fastener, or otherwise attached to the body of the first endplate or second endplate. The cap can also be integrated, deposited, or coated onto the surface of the body of the first endplate or second endplate.

The caps 1107, 1115, 1116 can include or be formed from bone growth inducing material and can include a variety of porous geometries or varying densities that promote bone growth through interdigitation. For example, the caps can be formed from silicon nitride or manufactured with a predetermined level of porosity to enable stiffness matching with surrounding bone and tissue and to facilitate bone growth. Moreover, the caps can be infused with bone growth factors to encourage rapid healing and bone ingrowth upon implantation of the intervertebral implant in the body. Bone growth factors may include, but are not limited to, bone morphogenic proteins, osteoconducting elements and compounds, collagen fibers, blood cells, osteoblast cells, and other suitable bone growth factors known in the art.

Figure 14:
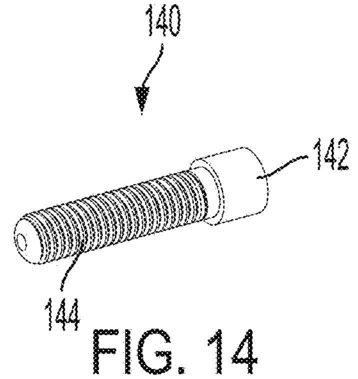
FIG. 14 is a perspective view of an auger of the expandable intervertebral implant of FIG. 1.
Figure 15:
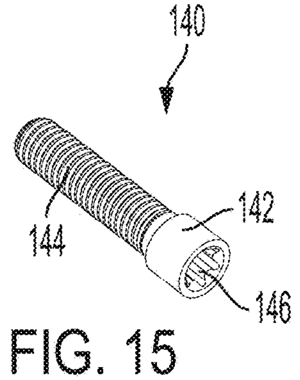
FIG. 15 is another perspective view of the auger of the expandable intervertebral implant of FIG. 1.

The auger 140 is configured as best shown in FIGS. 14 and 15 and includes a head 142 and a threaded body 144. The head 142 is completely contained between the first endplate 110 and second endplate 120 (FIG. 1) when the implant is in a fully assembled configuration. The head 142 of the auger includes a mating feature or drive 146 for engaging a driving tool (not shown). The head 142 is sized to have a larger diameter than a diameter of the threaded body so as to engage the flange 141 of the translation member, if necessary. A terminal end of the threaded body is concave in shape, i.e., a concave distal end or a distally facing concave end. The auger 140 can be formed from materials that contain osteoinductive, osteoconductive, and/or germicidal surface properties for promoting bone formation and tissue development, e.g., ceramics such as silicon nitride, zirconium oxide, silver oxide, and other suitable materials, and can also be formed from radiopaque or radiolucent materials.

Figure 16:
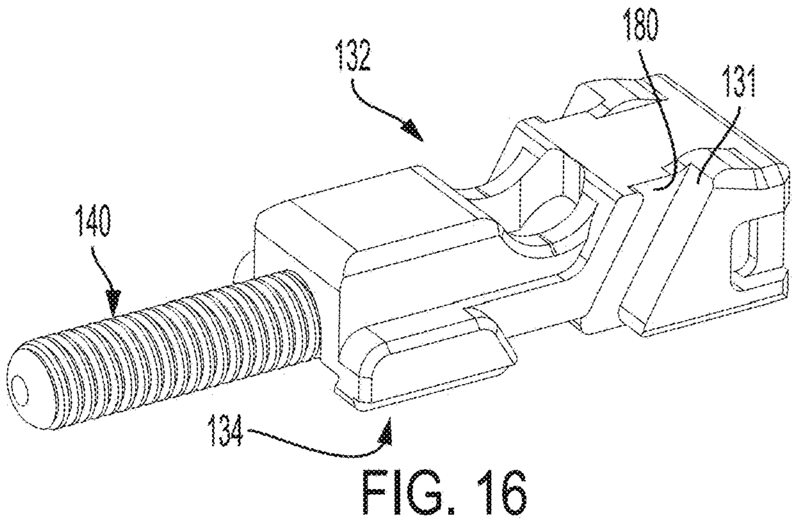
FIG. 16 is a perspective view of the translation member and auger of the expandable intervertebral implant of FIG. 1.
Figure 17:
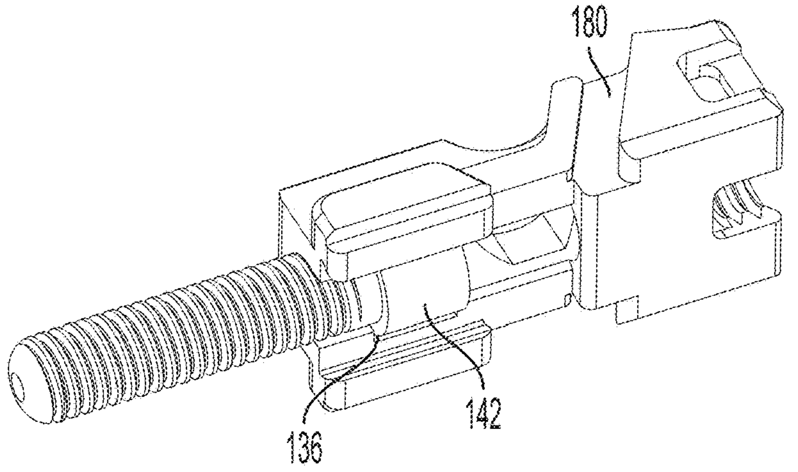
FIG. 17 is a bottom perspective view of the translation member and auger of the expandable intervertebral implant of FIG. 1.
Figure 18:
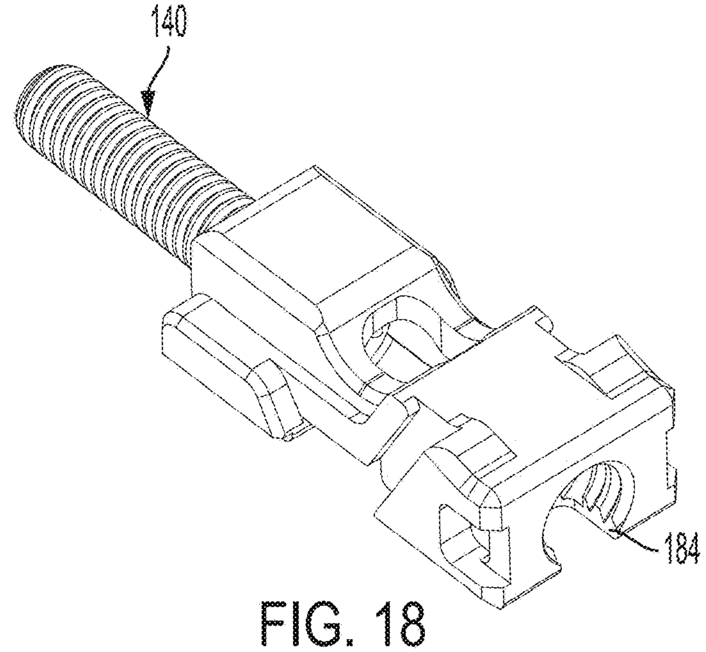
FIG. 18 is another perspective view of the translation member and auger of the expandable intervertebral implant of FIG. 1.

Referring now to FIGS. 16-18, the auger 140 is mounted within the translation member 130 substantially flush with the lower surface 134 of the translation member. Specifically, the translation member includes a recess 136 facing downwardly for mountably receiving the auger 140 including the head 142 therein. The head 142 is positioned within the recess 136 so as to be flush with the lower surface 134 of the translation member 130.

Figure 37:
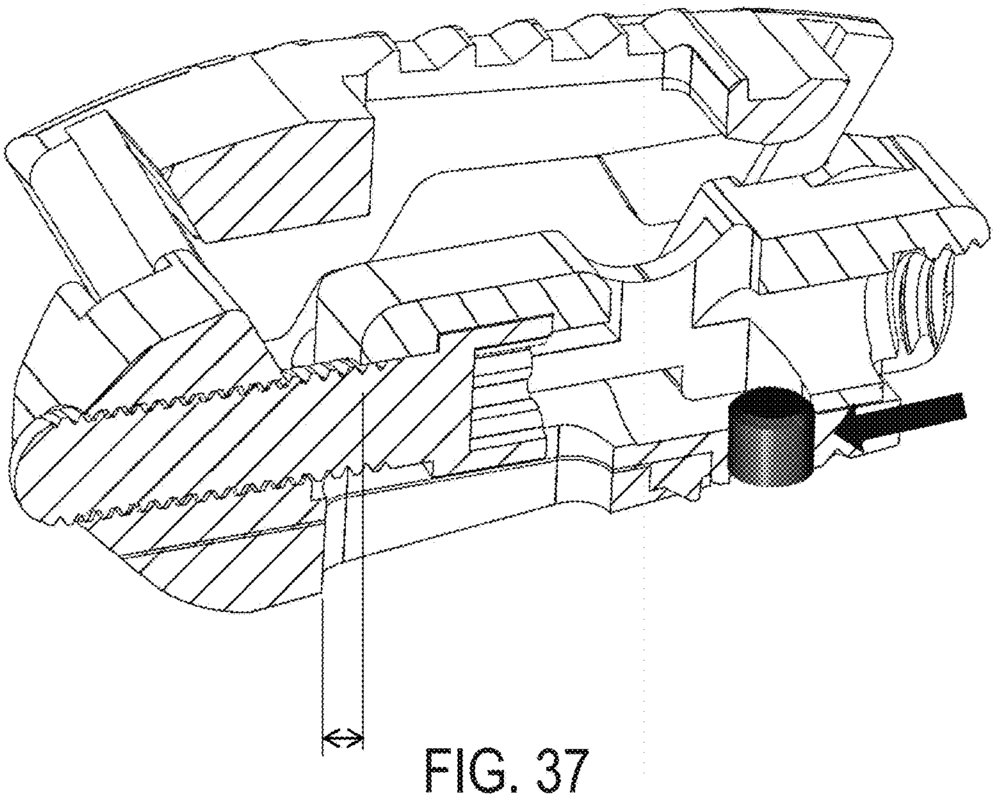
FIG. 37 is a perspective view of the fully assembled expandable intervertebral implant (shown in cross-section) of FIG. 1 with a stop element.

Referring to FIGS. 1A, 8 and 37, in accordance with an alternate exemplary embodiment, the second endplate 120 can include a stop 150 for operatively engaging the translation member 130 at a predetermined position. The stop 150 can be configured as a dowel or rod pin, and positioned within a recess 151 of the second endplate 120, and extends proud of the upper surface of the second endplate. During implantation, the stop 150 is pressed into the second endplate 120 recess after the implant is expanded to create a backstop in the event the auger breaks out i.e., moves anteriorly, after implantation. In sum, the stop 150 prevents the auger from breaking out of the implant.

Figure 38:
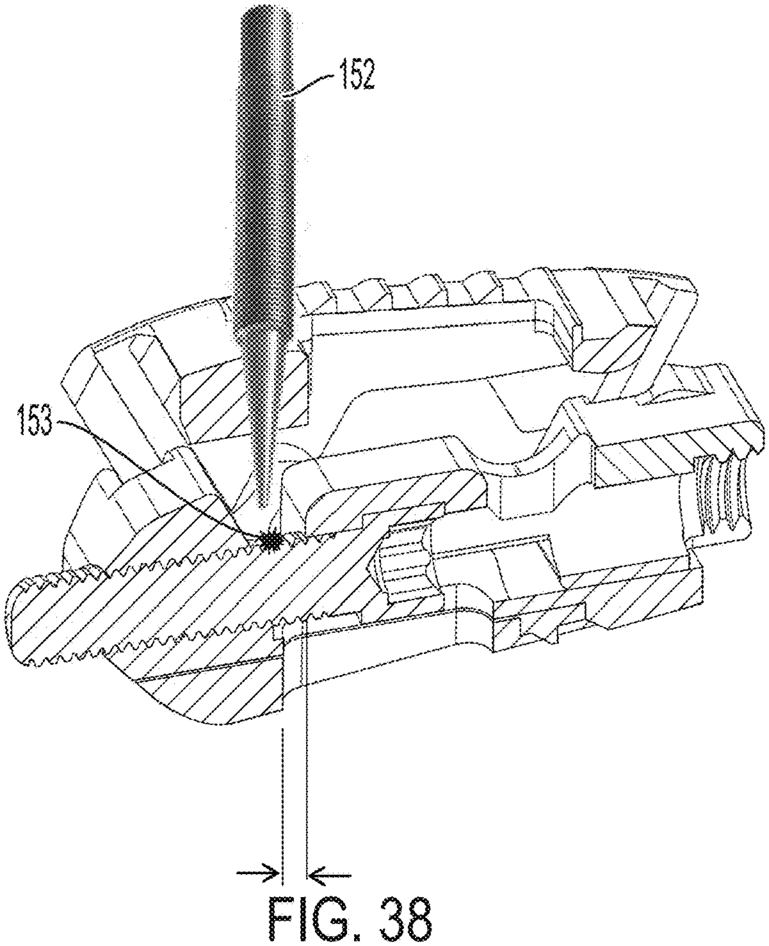
FIG. 38 is a perspective view of the fully assembled expandable intervertebral implant (shown in cross-section) of FIG. 1 with the auger being peened.

Alternatively, in lieu of a stop, the auger threads can include a peened thread or a bent thread, e.g., formed by a peening tool to form a stop on the auger after implantation. That is, a peening tool 152 (FIG. 38) is used to deform the auger threads 153 at a specific location to form a stop that prevents the translation member 130 from moving too far anteriorly into the posteriorly facing sloped surface 122 of the second endplate 120.

With reference to FIGS. 16-22, the expandable intervertebral implant 100 is assembled in a modular fashion. Specifically, as shown in FIGS. 16-18, the auger 140 is first mounted about the lower surface 134 of the translation member 130. That is, the head 142 of auger 140 is mounted within the recess 136 from the lower surface 134 of the translation member 130.

Figure 19:
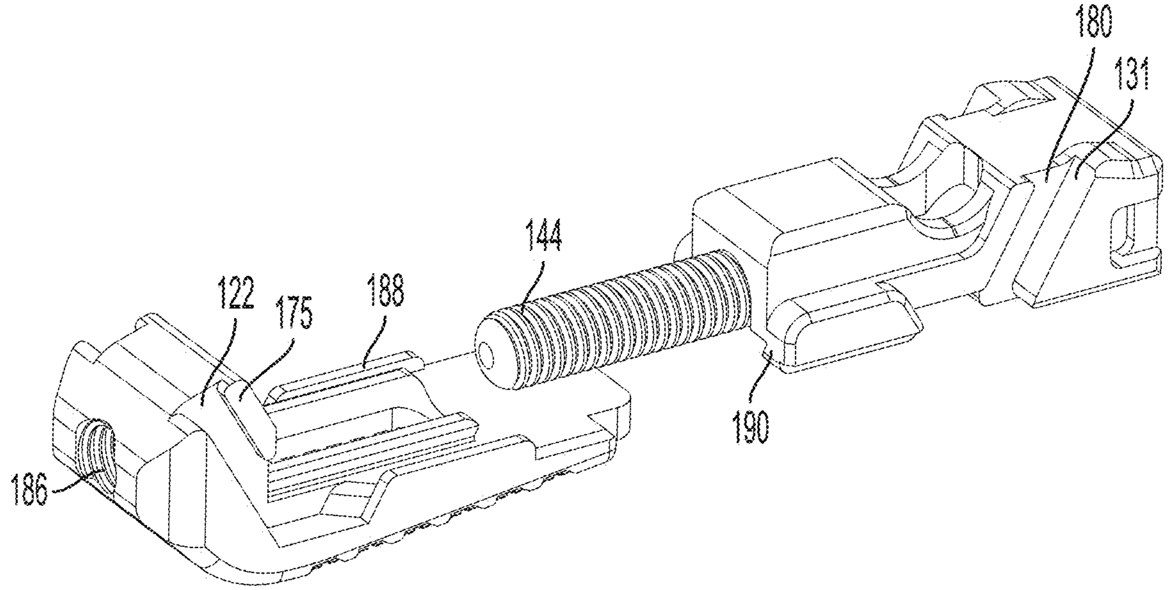
FIG. 19 is a perspective view of the translation member and auger for engaging the second endplate of the expandable intervertebral implant of FIG. 1.
Figure 20:
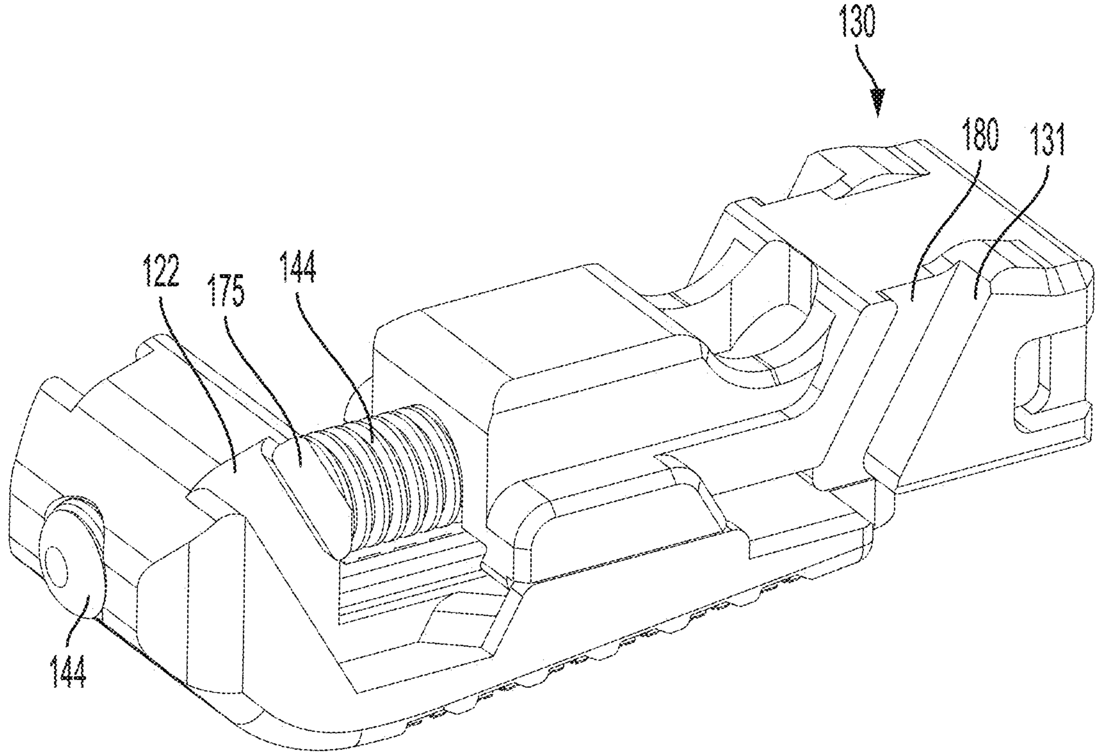
FIG. 20 is another perspective view of the translation member and auger attached to the second endplate of the expandable intervertebral implant of FIG. 1.

Thereafter, as shown in FIGS. 19 and 20, the threaded body 144 of the auger 140 engages the threads of through hole 186 of the second endplate 120. As the auger 140 engages the through hole 186, the retention track 188 of the second endplate 120 slideably engages the cooperating retention track 190 of the translation member 130. As such, the auger 140 and translation member 130 are operatively connected to the second endplate 120.

Figure 21:
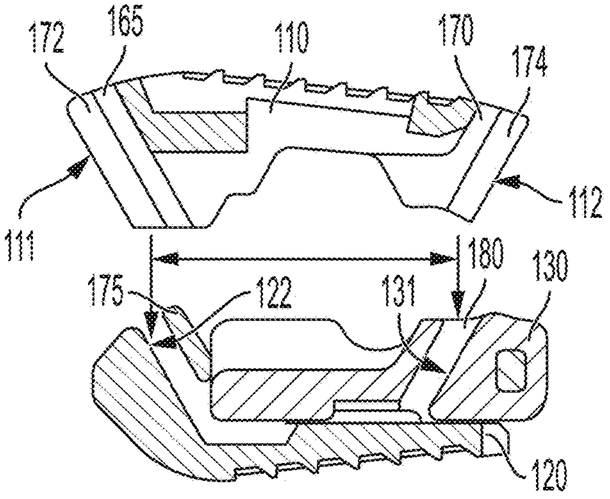
FIG. 21 is a side view of the first endplate slidably attaching to the translation member and second endplate (shown in cross-section) of the expandable intervertebral implant of FIG. 1.
Figure 22:
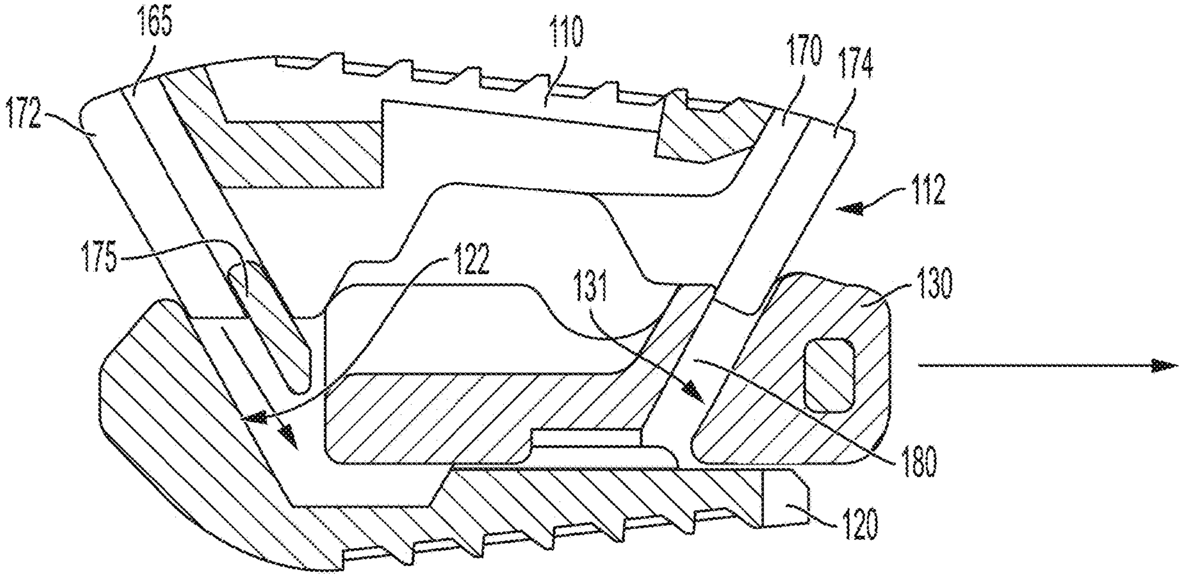
FIG. 22 is another side view of the first endplate slidably attaching to the translation member and second endplate (shown in cross-section) of the expandable intervertebral implant of FIG. 1.
Figure 23:
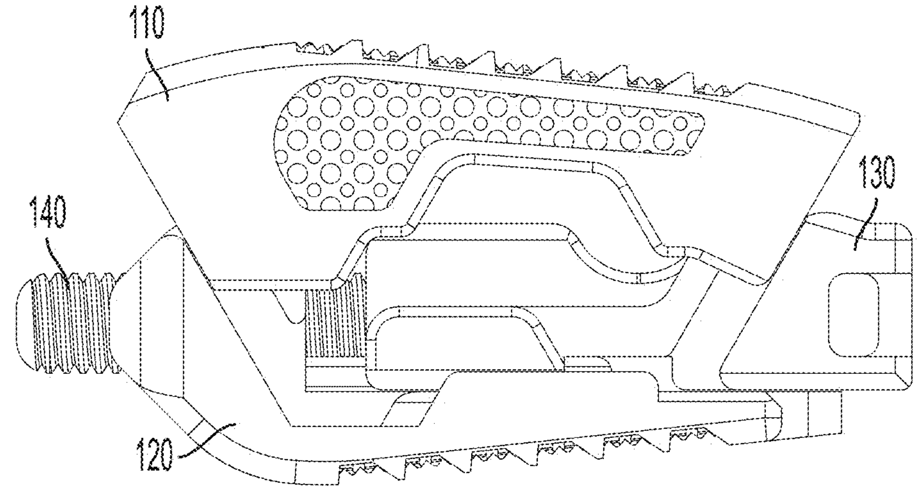
FIG. 23 is a side view of an assembled expandable intervertebral implant of FIG. 1.
Figure 23A:
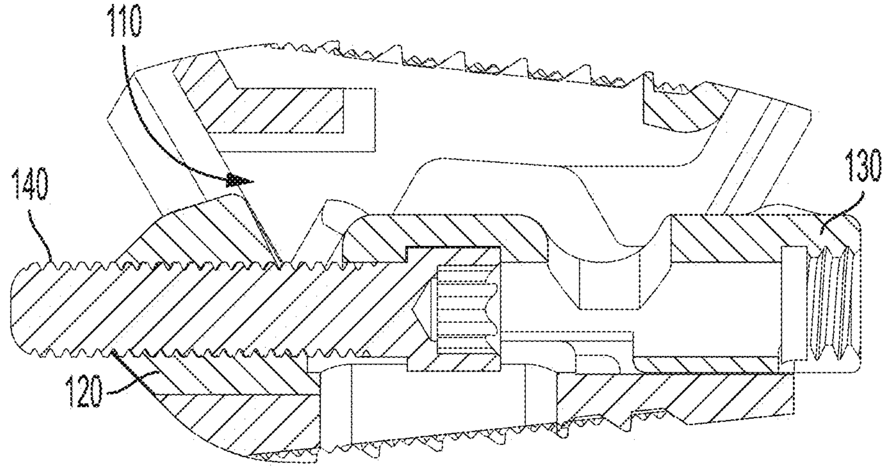
FIG. 23A is a cross-sectional side view of the assembled expandable intervertebral implant of FIG. 23.

Referring to FIGS. 21-23, to assemble the implant together, the first endplate 110 is positioned above the second endplate 120 and translation member 130. Specifically, the first endplate 110 is positioned such that the anterior male tongues 172 and posterior male tongues 174 of the first endplate 110 are respectively aligned with the posteriorly facing sloped surface 122 of the second endplate 120 and the anteriorly facing sloped surface 131 of the translation member 130, respectively. Thereafter, the first endplate 110 is lowered such that the respective lips of the anterior male tongue 172 and posterior male tongue 174 engage the female grooves of the posteriorly facing sloped surface 122 of the second endplate 120 and the anteriorly facing sloped surface 131 of the translation member 130.

Figure 24:
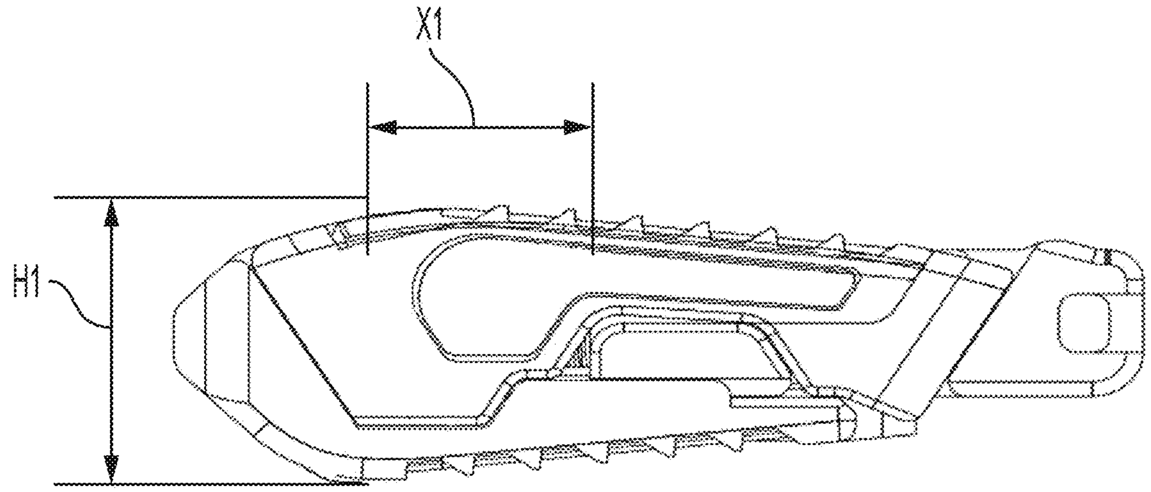
FIG. 24 is a side view of the expandable intervertebral implant of FIG. 1 in a collapsed or non-expanded position.
Figure 25:
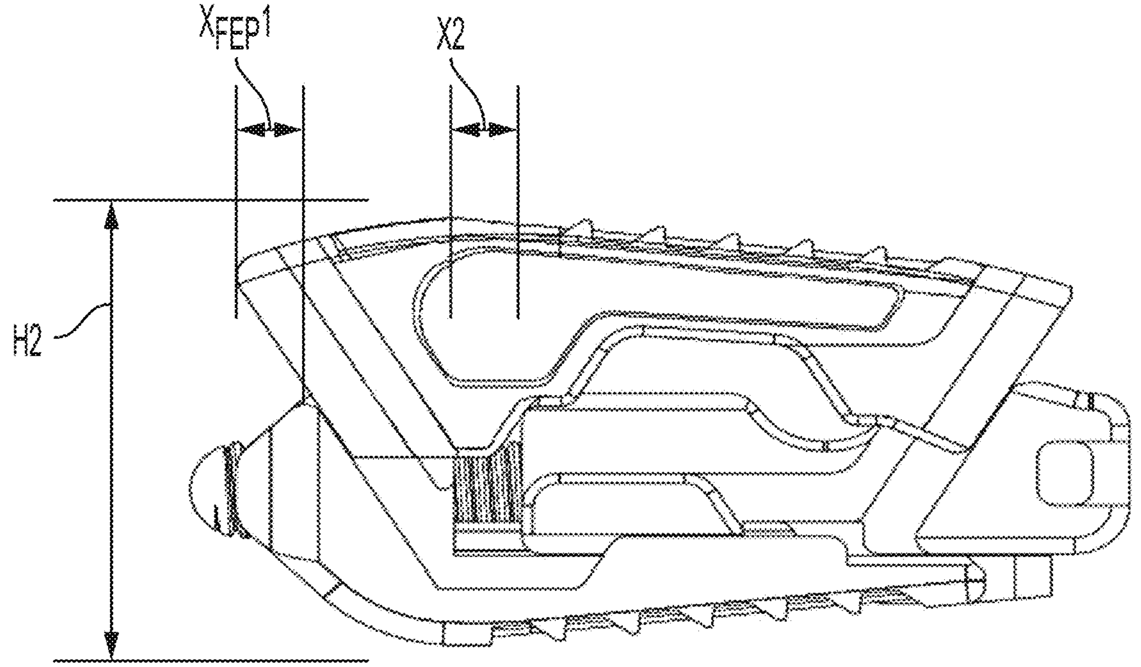
FIG. 25 is a side view of the expandable intervertebral implant of FIG. 24 in an expanded position.
Figure 26:
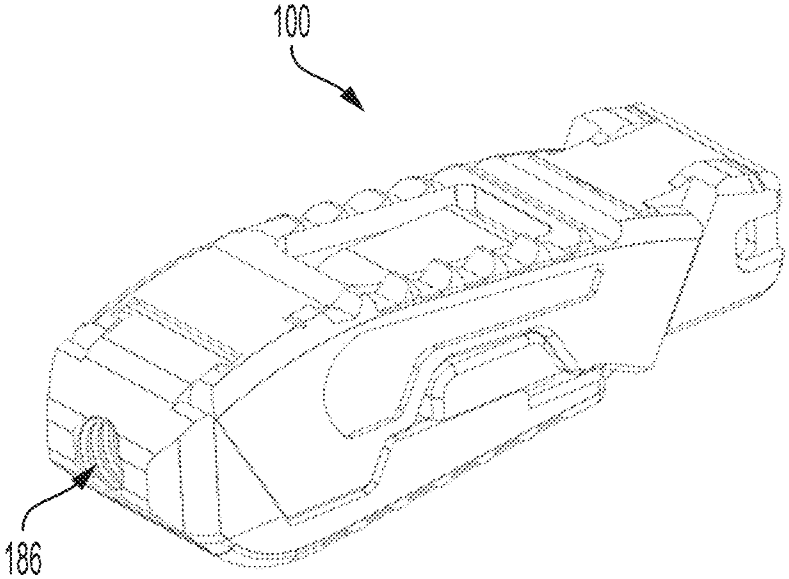
FIG. 26 is an anterior perspective view of the expandable intervertebral implant of FIG. 1 in a collapsed position.
Figure 27:
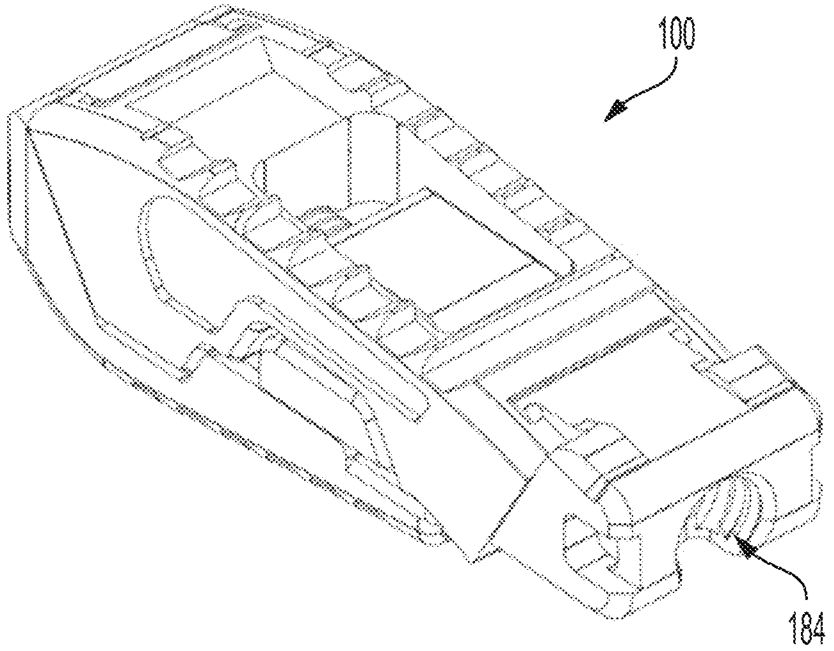
FIG. 27 is a posterior perspective view of the expandable intervertebral implant of FIG. 1 in a collapsed position.
Figure 28:
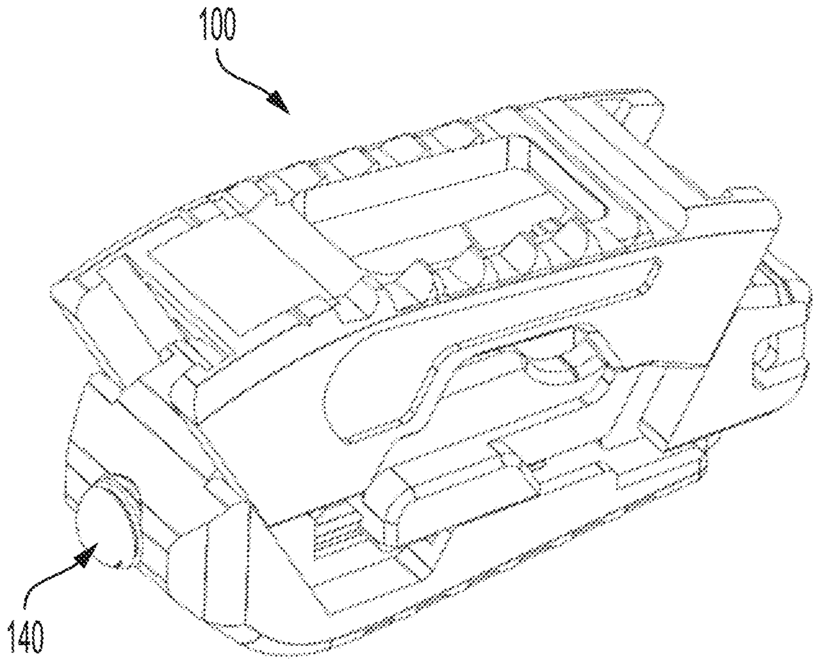
FIG. 28 is an anterior perspective view of the expandable intervertebral implant of FIG. 1 in an expanded position.
Figure 29:
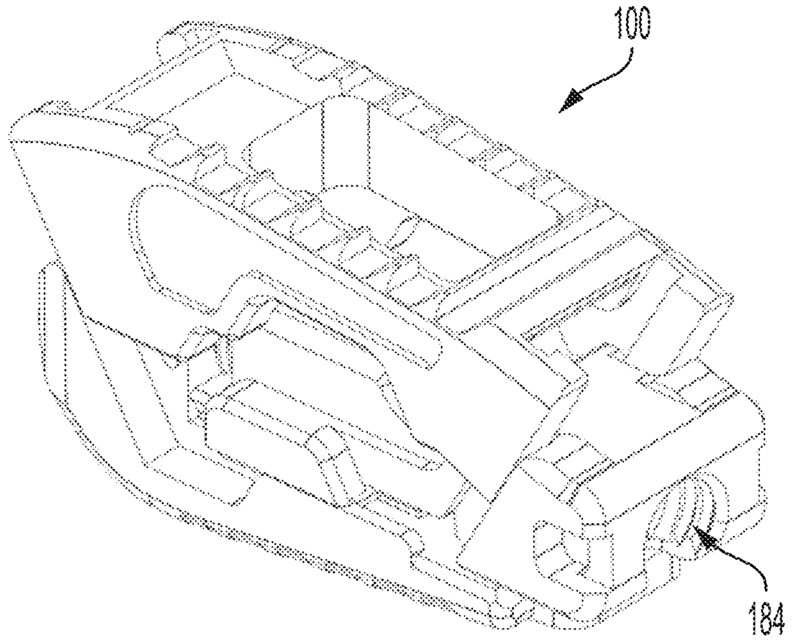
FIG. 29 is a posterior perspective view of the expandable intervertebral implant of FIG. 1 in an expanded position.

The expandable intervertebral implant 100 can advantageously transition between a collapsed configuration (FIGS. 24, 26 and 27) and an expanded configuration (FIGS. 25, 28 and 29). That is, the first endplate 110 is movable relative to the second endplate 120 between a collapsed first position (FIGS. 24, 26 and 27) and an expanded second position (FIGS. 25, 28 and 29). In the collapsed configuration, for example, as illustrated in FIG. 24, the implant 100 is at a first height H1 (e.g., as measured from the upper surface 113 of the first endplate 110 to the lower surface 126 of the second endplate 120). In the expanded configuration, for example, as illustrated in FIG. 25, the implant 100 expands to a second height H2 that is greater than H1. Further, in the second position or expanded position, the first endplate is anteriorly spaced from the first position or the second endplate.

In operation, a rotational force applied on the auger 140 causes the threaded body 144 of the auger to engage the through hole 186 of the second endplate 120 to translate the translation member 130 relative to the second endplate 120. That is, in the collapsed position (FIG. 24), the translation member 130 is at a first distance X1 (e.g., measured gap between a posteriorly facing side of the second endplate 120 and the anterior end 137 of the translation member 130). In the expanded position (FIG. 25), the translation member 130 is at a second distance X2 that is less than X1. As the distance between the translation member 130 and second endplate 120 decreases (X1→X2), the height between the first endplate 110 and second endplate 120 increases (H1→H2), and the anterior end of the first endplate moves anteriorly a distance $X_{FEP}$1 relative to the anterior end position of the first endplate in the collapsed position.

In some exemplary embodiments, the second height H2 can be from about 25% to 100% greater than the first height H1, including 30, 40, 50, 60, 70, 80 and 90%. In other exemplary embodiments, the second height H2 can be from about 50% to 100% greater than the first height H1. In other embodiments, the second height H2 can be from at least about 50% greater than the first height H1. For example, the second height H2 can be about 4 mm to 6 mm including 4.5, 5, and 5.5 mm greater than the first height H1, but also less than 4 mm and greater than 6 mm. Generally, the change in height is caused by movement of the first endplate 110 and the second endplate 120 towards and/or away from each other. Those skilled in the art may appreciate that, in use, the height of the expandable intervertebral implant 100 can be adjusted to accommodate an individual patient's needs.

Referring back to FIGS. 19-22, in operation the auger 140 is threadably engaged to the through hole 186 of the second endplate 120. A driving tool can be engaged to the mating feature 146 of the auger 140 in order to move the implant 100 into the expanded position. A rotational force applied to the driving tool rotates the auger 140 in a first direction, which in turn causes the threaded body 144 to further engage the through hole 186 of the second endplate 120, translating the translation member 130 relative to the second endplate 120. As the translation member 130 and the second endplate 120 translate towards each other, the respective mating elements of the translation member 130 and/or the second endplate 120 push against corresponding complementary mating elements on the first endplate 110, thereby pushing the first and second endplates 110, 120 apart and increasing the overall height of the implant 100. Further, if the auger 140 is rotated in a second direction opposite the first direction, the auger moves away from the second endplate 120 thereby allowing the first endplate to move downwardly. Thus, those skilled in the art may appreciate that the intervertebral implant 100 may be reversibly expandable and/or collapsible.

In general, as the intervertebral implant 100 adjustably moves back and forth between the expanded and the collapsed position, the sloped anterior face 111 of the first endplate 110 matingly engages the posteriorly facing sloped surface 122 of the second endplate 120. Similarly, the sloped posterior face 112 of the first endplate 110 matingly engages the anteriorly facing sloped surface 131 of the translation member 130. As the respective posteriorly facing sloped surface 122 and the anteriorly facing sloped surface 131 push against the corresponding sloped anterior and posterior faces 111, 112 of the first endplate 110, the first and second endplates 110, 120 are pushed apart to the expanded position.

Figure 33:
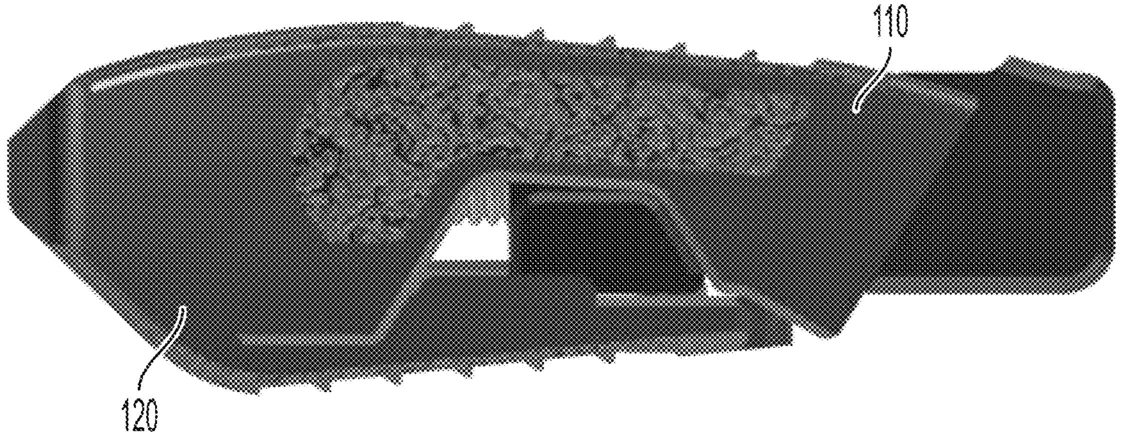
FIG. 33 is a side view of the expandable intervertebral implant of FIG. 1 in a collapsed position having a textured surface.
Figure 34:
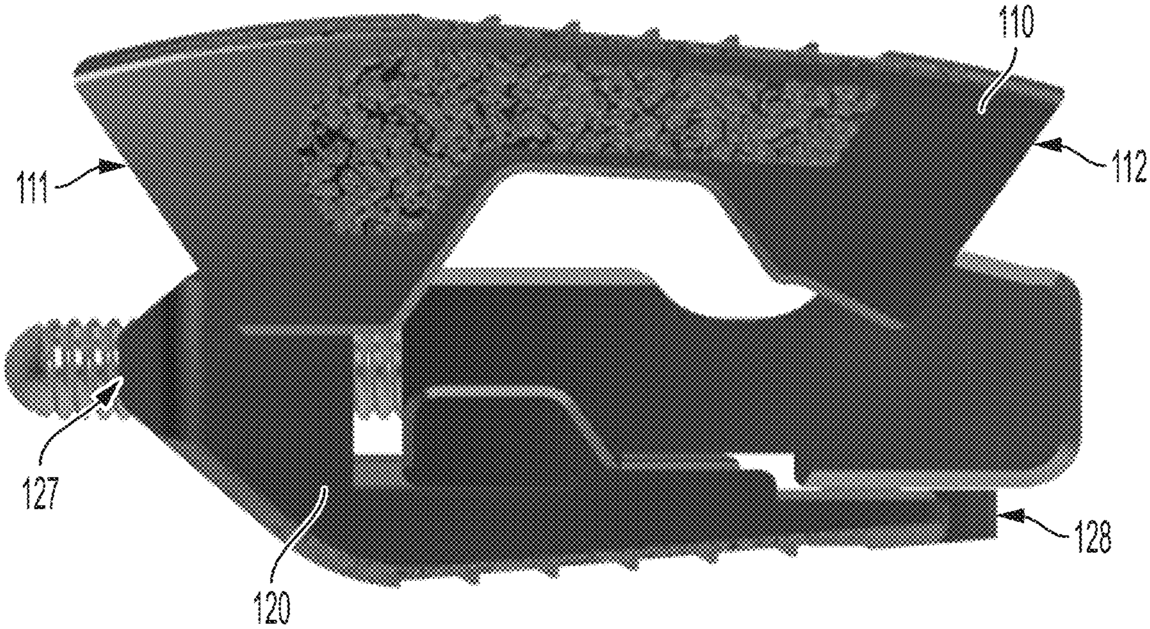
FIG. 34 is a side view of the expandable intervertebral implant of FIG. 33 in an expanded position.
Figure 41:
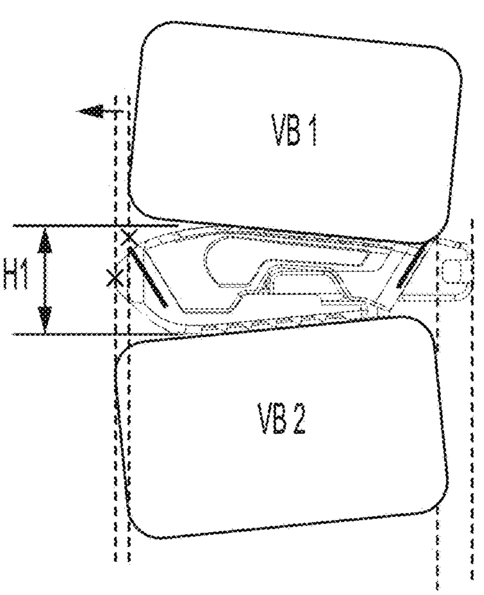
FIG. 41 are side views of the expandable intervertebral implant of FIG. 1 in the collapsed position and the expanded position.

As shown in FIGS. 33 and 34, as the intervertebral implant moves from the collapsed position (FIG. 33) to the expanded position (FIG. 34), translation occurs between the first endplate 110 and the second endplate 120 to create a gap. In the expanded position, the sloped anterior face 111 of the first endplate 110 extends further anteriorly than the anterior end 127 of the second endplate 120. Similarly, in the expanded position, the sloped posterior face 112 of the first endplate 110 extends further posteriorly than the posterior end 128 of the second endplate 120. As a result, when the intervertebral implant 100 moves from the collapsed position to the expanded position, translation occurs between the first endplate 110 and the second endplate 120 in both a vertical and horizontal direction (see FIG. 25). Advantageously, translation of one of the first endplate 110 and the second endplate 120 in the horizontal direction e.g., the A-P direction, relative to the other is beneficial for the correction of spinal misalignment associated with Grade 1 spondylolisthesis. For example, as shown in FIG. 41, the horizontal translation of the first endplate 110 relative to the second endplate 120 may accommodate for minor spinal misalignment owing to the horizontal A-P translation and/or surface profile of the top surface of the first endplate. Specifically, upon vertical translation of the first endplate 110 relative to the second endplate 120, the height between the first endplate 110 and second endplate 120 increases (H1→H2), and vertebrae (VB1) moves anteriorly a distance X3 relative to the anterior end position of vertebrae (VB1) which remains in a fixed stationary position. That is, as vertebrae (VB1) is anchored to the first endplate 110, the first endplate 110 and vertebrae (VB1) collectively move anteriorly a distance X3 relative to the second endplate.

Figure 47:
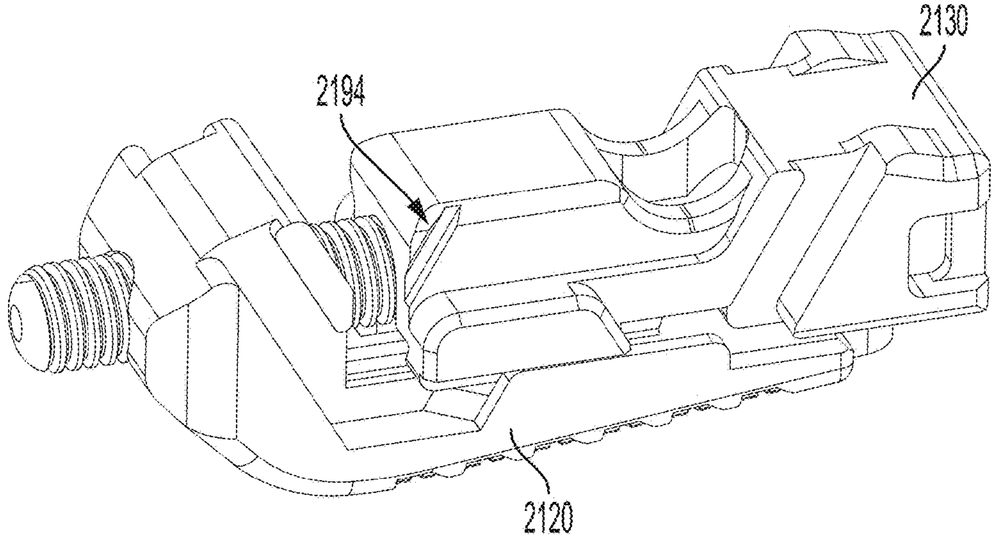
FIG. 47 is a perspective view of the translation member and auger attached to a second endplate of the expandable intervertebral implant of FIG. 44.

Referring now to FIGS. 44-47, in accordance with another exemplary embodiment, the subject disclosure provides an expandable intervertebral implant 2100 that includes a first endplate 2110 and a translation member 2130 having additional mating elements, i.e., supplementary posterior track 2192 on the first endplate 2110 (FIG. 46) and supplementary anterior track 2194 on the translation member 2130 (FIG. 47). The expandable intervertebral implant 2100 is similar to expandable intervertebral implant 100 except as specifically described herein. The supplementary posterior track 2192 is configured as a tongue. However, it can alternatively be configured as any other similar element including, but not limited to, a ridge, tooth or projection. Similarly, the supplementary anterior track 2194 is configured as a recess. However, it can be alternatively configured as any other similar element including, but not limited to, a groove or channel. When assembled, the supplementary posterior track 2192 on the first endplate 2110 slideably or slidingly engages the supplementary anterior track 2194 on the translation member 2130.

The additional mating elements on the first endplate 2110 and translation member 2130 provide additional stability to the intervertebral implant 2100 during assembly. Specifically, when the components of the intervertebral implant, i.e., first endplate 2110 and translation member 2130, have a longer longitudinal length, there is a potential for buckling and/or jamming to occur. The addition of the supplementary posterior track 2192 on the first endplate 2110 and more particularly about a midportion of the first endplate, and its complementary supplementary anterior track 2194 on the translation member counters the forces that can potentially impart buckling and/or jamming. In other words, the additional mating elements allow for larger constructions of the intervertebral implant by addressing the adverse effects of buckling and binding during assembly. In accordance with an aspect, the supplementary posterior track 2192 and supplementary anterior track 2194 can each be configured as a pair of tracks on opposite sides of their respective components to provide additional stability to the intervertebral implant.

Figure 48:
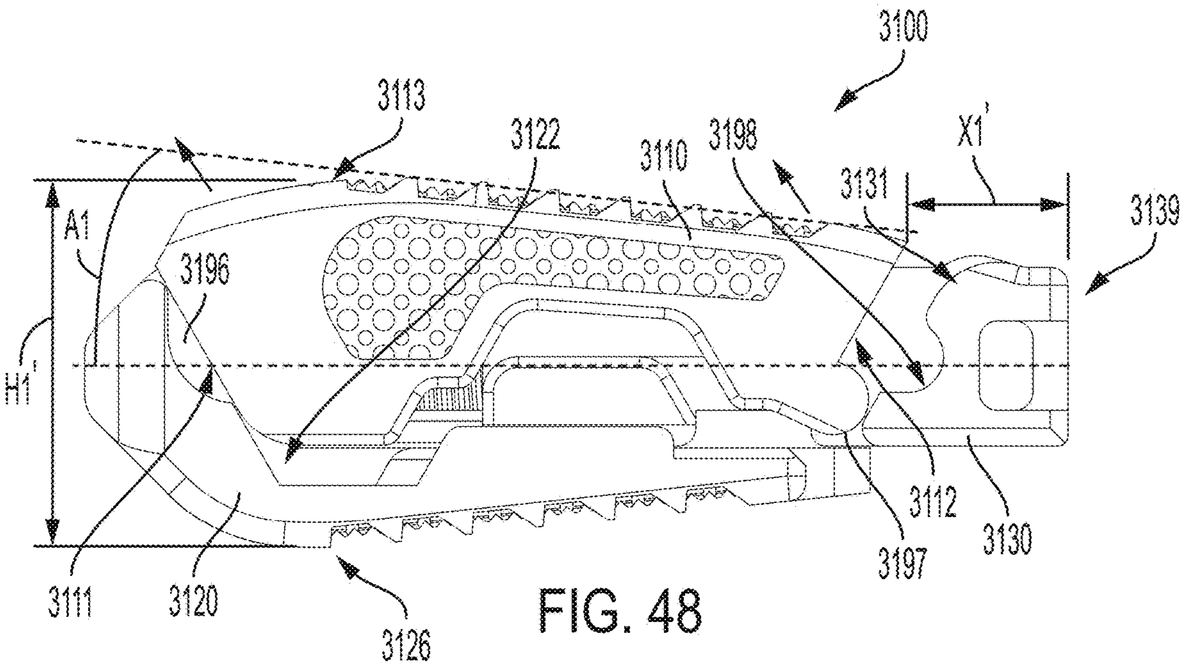
FIG. 48 is a side view of an expandable intervertebral implant in accordance with yet another exemplary embodiment of the subject disclosure in a collapsed position.
Figure 49:
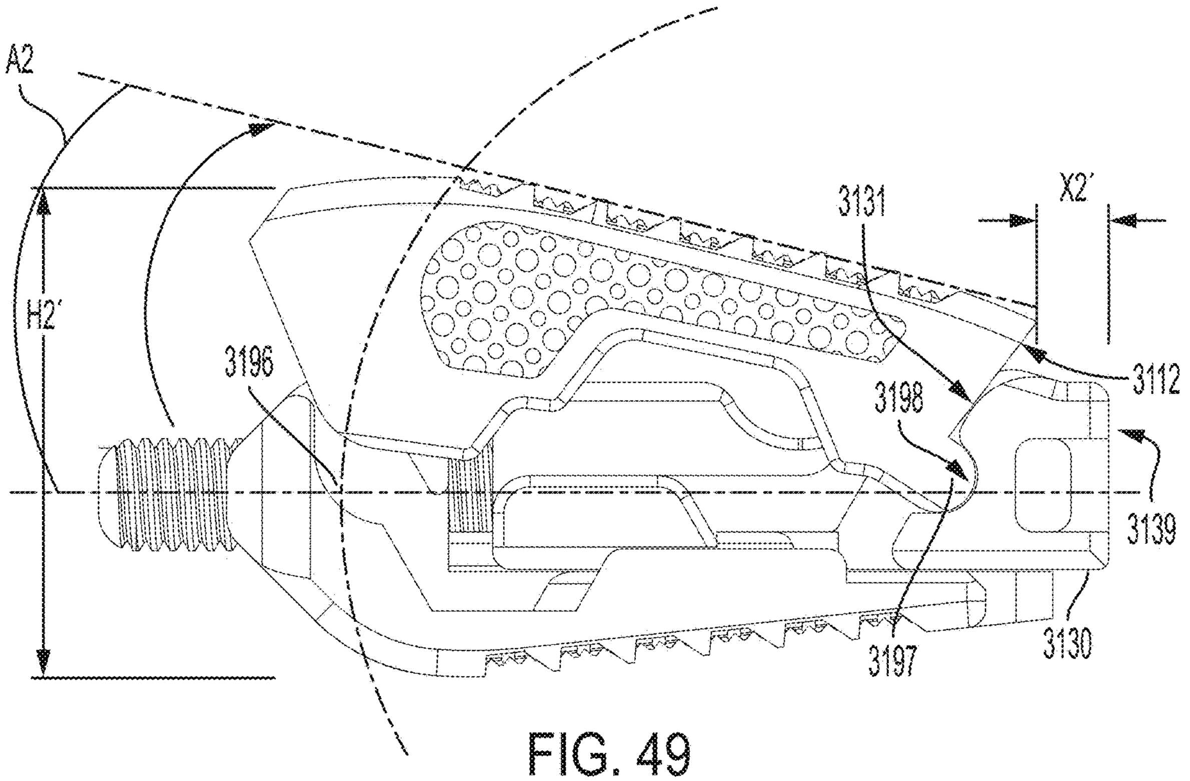
FIG. 49 is a side view of the expandable intervertebral implant of FIG. 48 in an expanded position.
Figure 50:
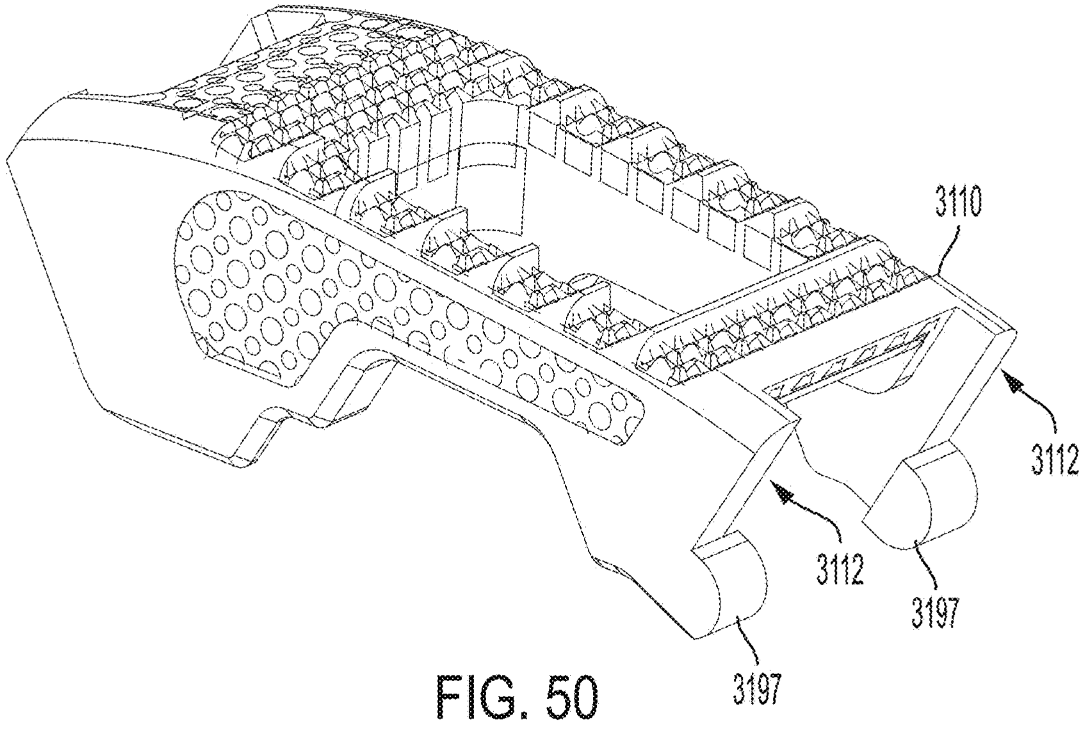
FIG. 50 is a perspective view of a first endplate of the expandable intervertebral implant of FIG. 48.
Figure 51:
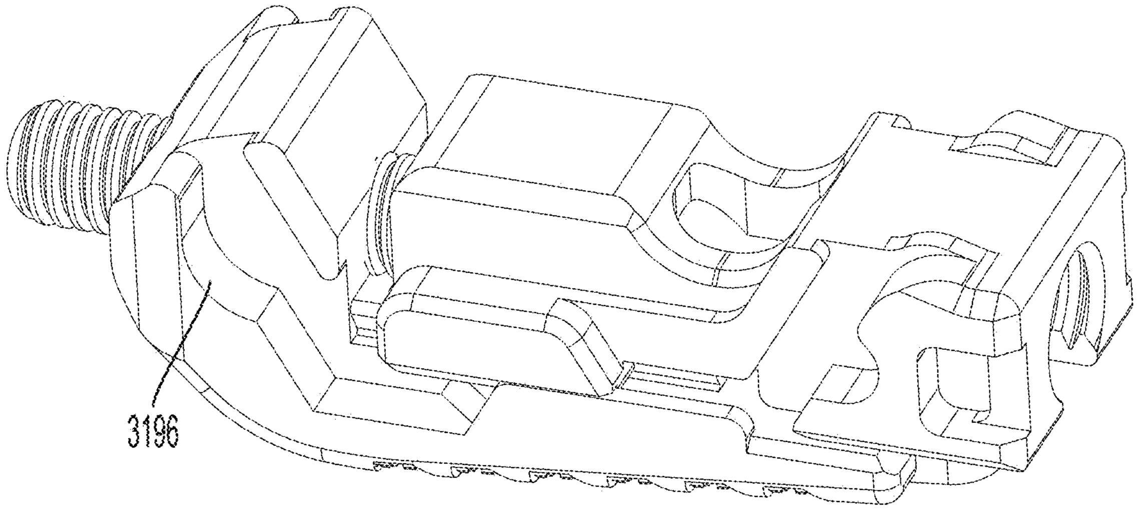
FIG. 51 is a perspective view of a translation member and auger attached to a second endplate of the expandable intervertebral implant of FIG. 48.
Figure 52:
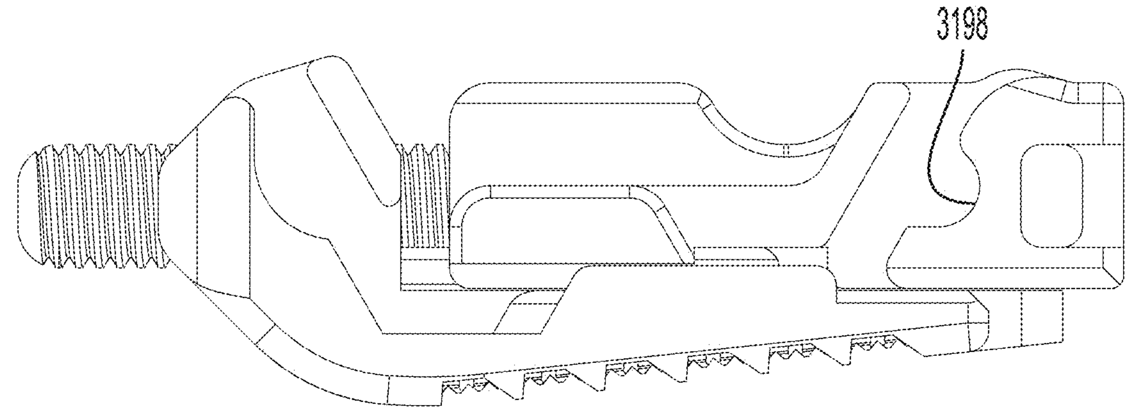
FIG. 52 is a side view of the translation member and auger attached to the second endplate of the expandable intervertebral implant of FIG. 48.
Figure 53A:
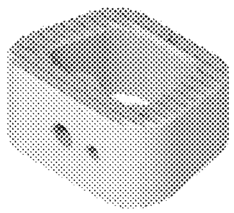
FIGS. 53A-E are perspective views of various footprints of interbody fusion devices applicable for use with the subject disclosure.
Figure 53B:
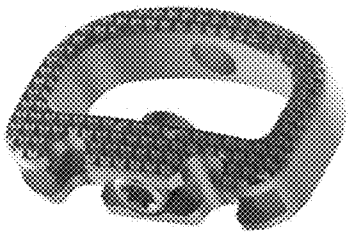
Figure 53C:
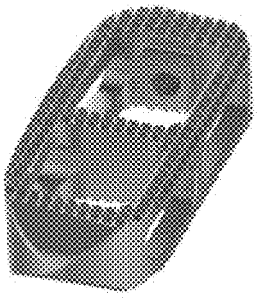
Figure 53D:
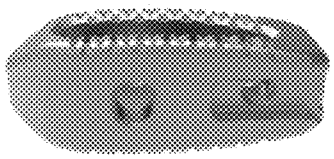
Figure 53E:
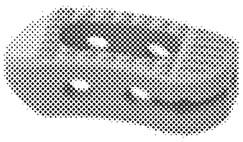

Referring now to FIGS. 48-52, in accordance with another exemplary embodiment, the subject disclosure provides for an expandable intervertebral implant 3100. The expandable intervertebral implant 3100 is similar to expandable intervertebral implant 100 except as specifically described herein. The expandable intervertebral implant 3100 includes a posteriorly facing sloped surface 3122 of a second endplate 3120 that comprises a recess 3196 to facilitate angular expansion of the intervertebral implant 3100 when the posteriorly facing sloped surface 3122 matingly engages a sloped anterior face 3111 of a first endplate 3110 during assembly. The expandable intervertebral implant 3100 also includes a translation member 3130 having a recess or radial recess 3198 about its anteriorly facing sloped surface 3131 for facilitating angular expansion of the intervertebral implant 3100. Specifically, as shown in FIGS. 48-50, a sloped posterior face 3112 of the first endplate 3110 includes a radial hinge, e.g., a radial protrusion 3197, that is received within the recess 3198 during assembly.

The first endplate is movable relative to the second endplate between a collapsed first position and an expanded second position similar to expandable intervertebral implant 100 (see e.g., FIGS. 24-29). As shown in FIGS. 48-52, the expandable intervertebral implant 3100 can advantageously transition between a collapsed configuration (FIG. 48) and an expanded configuration (FIG. 49) to achieve a lordotic angular expansion of the intervertebral implant 3100. In the collapsed configuration, for example, as illustrated in FIG. 48, the implant 3100 is at a first height H1' (e.g., as measured from the upper surface 3113 of the first endplate 3110 to the lower surface 3126 of the second endplate 3120) and creates an angle A1 between a longitudinally extending axis of the translation element 3130 and the upper surface 3113 of the first endplate 3110.

In the angularly expanded configuration, for example, as illustrated in FIG. 49, the implant 3100 expands to a second height H2' that is greater than H1' and creates an angle A2 that is greater than angle A1. In the collapsed position (FIG. 48), the translation member 3130 is at a first distance X1' (e.g., measured gap between the sloped posterior face 3112 of the first endplate 3110 and the posterior end 3139 of the translation member 3130). In the expanded position (FIG. 49), the translation member 3130 is at a second distance X2' that is less than X1'. As the distance between the translation member 3130 and second endplate 3120 decreases (X1'→X2'), the height between the first endplate 3110 and second endplate 3120 increases (H1'→H2') and the angle between the longitudinally extending axis of the translation element 3130 and the upper surface 3113 of the first endplate 3110 increases (A1→A2).

In sum, as a rotational force is applied to the auger, the translation member 3130 is translated relative to the second endplate 3120. As the translation member 3130 and the second endplate 3120 translate towards each other, the respective mating elements of the translation member 3130 and/or the second endplate 3120 push against corresponding complementary mating elements on the first endplate 3110, thereby pushing the first and second endplates 3110, 3120 apart and increasing the overall height of the implant 3100. Specifically, as the sloped anterior face 3111 of the first endplate 3110 matingly engages the posteriorly facing sloped surface 3122 of the second endplate 3120, the first endplate 3110 slides upward causing the height to increase. As the translation member 3130 is translated toward the second endplate 3120, the radial hinge 3197 of the first endplate 3110 moves upward and is received within the recess 3198 of the translation member 3130. As a result, continuing movement of the translation member 3130 towards the second endplate 3120 causes an anterior side of the first endplate 3110 to rise from angle A1 to angle A2. This movement is facilitated by interaction of the first endplate with the radial recess 3196 on the second endplate 3120.

While the subject disclosure discusses several exemplary embodiments of an expandable intervertebral implant, the expandable intervertebral implants discussed herein can be used with or in combination with various other interbody fusion devices such as those shown in FIGS. 53A-53E having various footprints including, but not limited to, transforaminal lumbar interbody fusion (TLIF), anterior lumbar interbody fusion (ALIF), lateral lumbar interbody fusion (LLIF), oblique lumbar interbody fusion (OLIF), posterior lumbar interbody fusion (PLIF), direct lateral interbody fusion (DLIF), curved transforaminal lumbar interbody fusion (curved TLIF), and anterior cervical interbody fusion (ACIF). The various footprints can have e.g., a width ranging from 8 mm to 45 mm, a length ranging from 20 mm to 65 mm, and a height ranging from 5 mm to 25 mm. Moreover, the intervertebral implant described herein can be used with a secondary cage that can be a TLIF, ALIF, LLIF, OLIF, PLIF, DLIF, curved TLIF, or ACIF device. Such cages are disclosed in U.S. Pat. No. 10,543,101 and 10,219,912, the disclosures of which are hereby incorporated by reference in their entirety for all purposes.

The subject disclosure also provides a method of manufacturing an endplate implant of an expandable intervertebral implant. The method includes creating a computer aided design (CAD) endplate model of an endplate implant having a sloped anterior face, a sloped posterior face, and superior face. An exemplary implant made can be an implant CAD model of implant 100, 1100, 2100. The sloped anterior face is angled greater than 10 degrees from the superior face. The method further includes the step of additively manufacturing the endplate implant based on the CAD endplate model with successive layers substantially parallel to the sloped anterior face. Advantageously, the layers being substantially parallel to the plane of the sloped anterior face provides significant strength to the implant when normal loads are applied to the first endplate.

Figure 36:
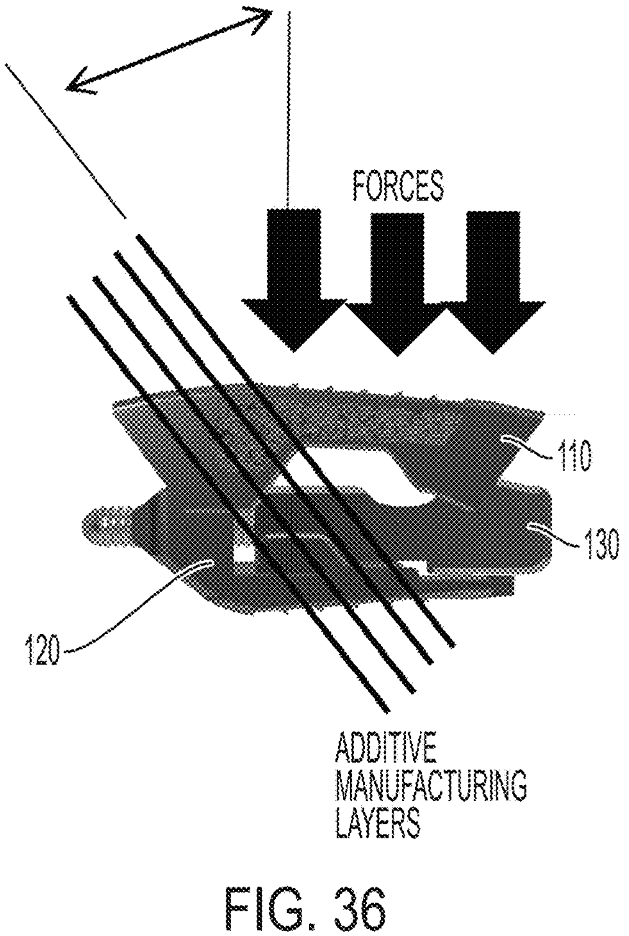
FIG. 36 is a side view of the expandable intervertebral implant of FIG. 1 in an expanded position illustrating loads applied to the implant along with lines depicting the layers formed by additive manufacturing of the implant.
Figure 39:
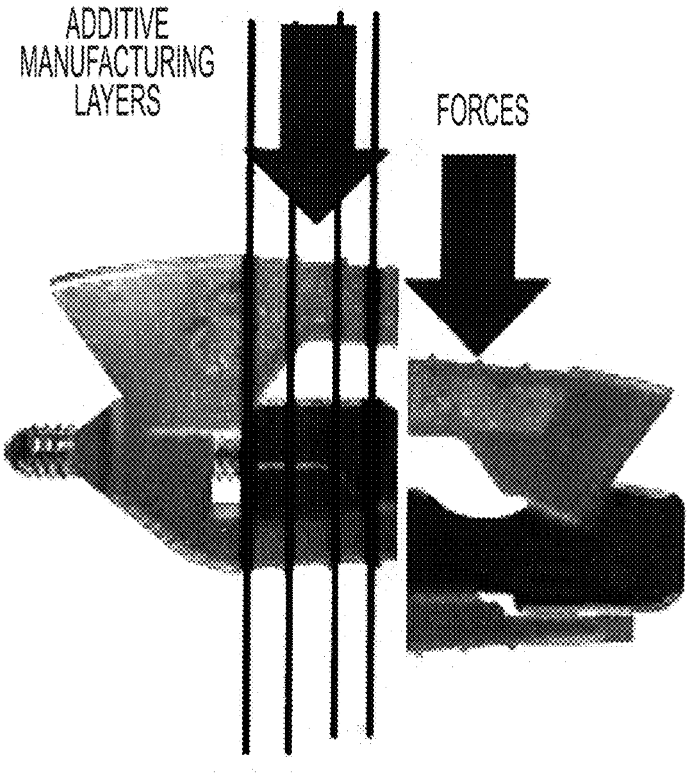
FIG. 39 is another side view of the expandable intervertebral implant of FIG. 1 in an expanded position illustrating loads applied to the implant along with lines depicting the layers formed by additive manufacturing of the implant in an undesirable orientation.
Figure 40:
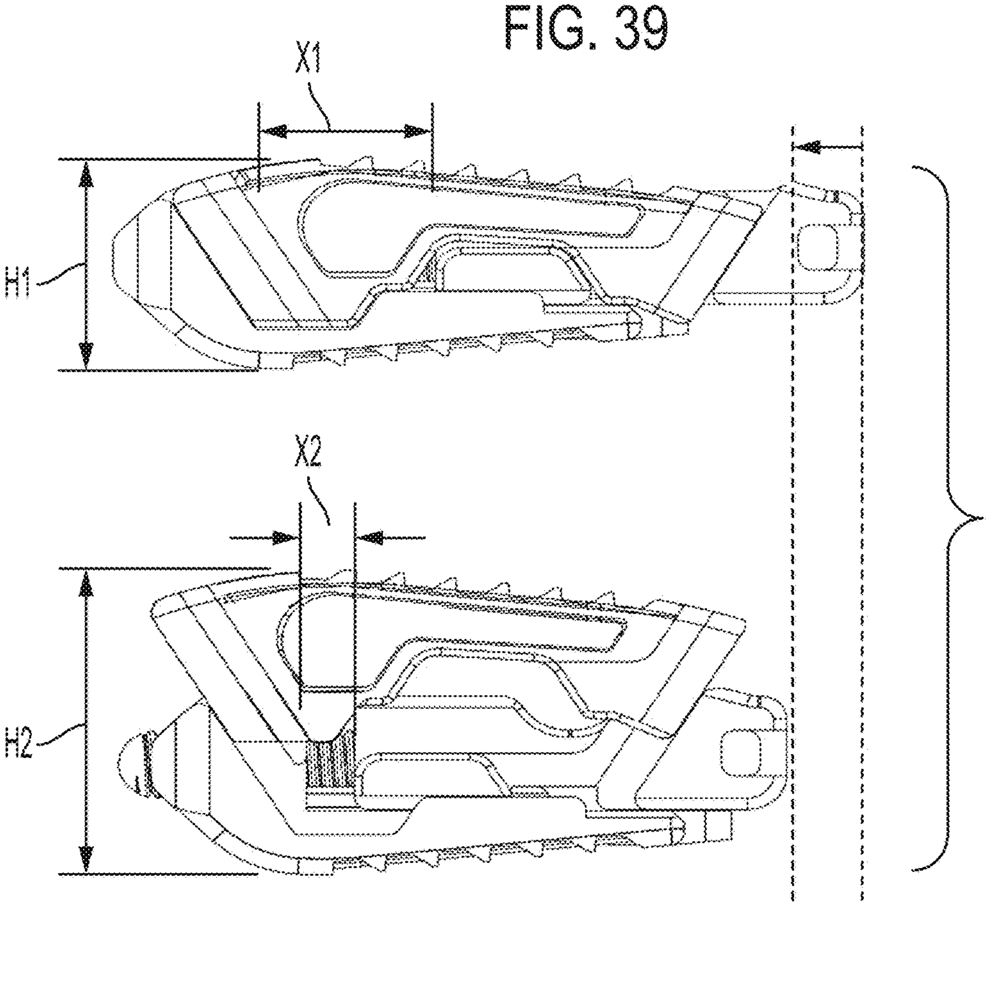
FIG. 40 are side views of the expandable intervertebral implant of FIG. 1 in a collapsed position and an expanded position.

As shown in FIGS. 36 and 39, during the step of additively manufacturing components of the expandable intervertebral implant, if the additive layers extend in a direction in line with forces normal to a longitudinal length of the implant (FIG. 39), the expandable intervertebral implant may shear easily. That is, the additive layers shown in FIG. 39 may cause failure due to parallel alignment between load forces and the additive layers. However, if the additive layers extend at an angle (FIG. 36), such as substantially parallel to the plane of the sloped anterior face or angled relative to a longitudinal length of the implant, the line of forces acting on the implant will be transverse to the additive layers, thereby reducing the likelihood of shearing of the implant.

Figure 35:
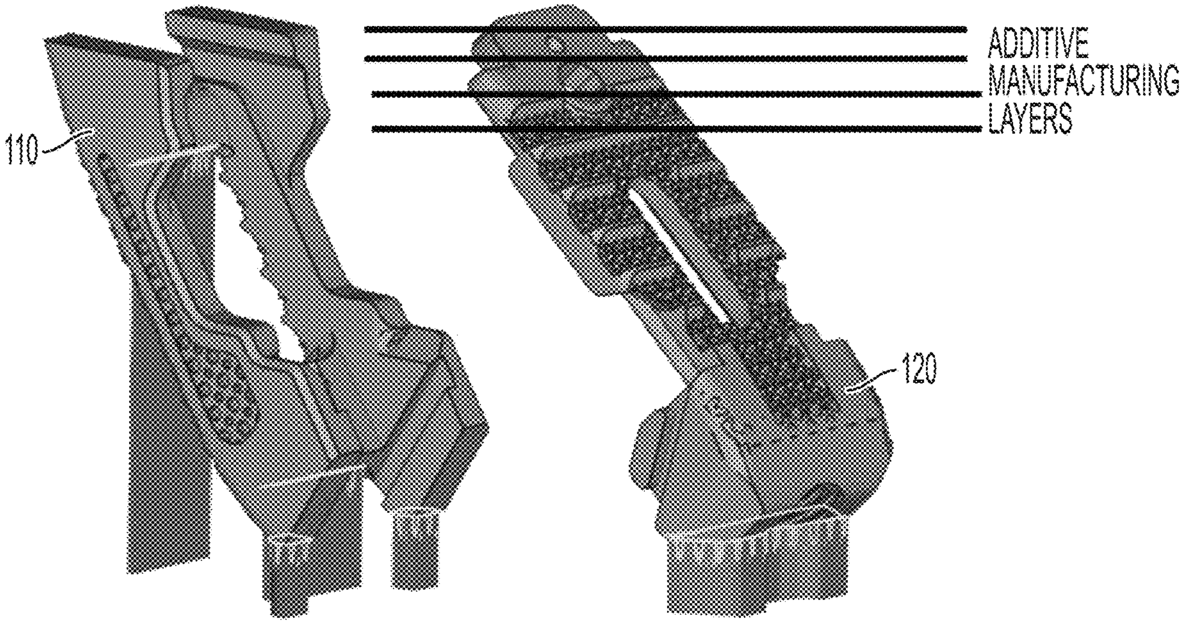
FIG. 35 is a perspective view of the first endplate and second endplate of the expandable intervertebral implant of FIG. 1 with lines depicting the layers formed by additive manufacturing of the implant.

Additive manufacturing allows the expandable intervertebral implant to be formed as a single integral piece and constructed layer-by-layer, bottom-to-top, such that the components are integrally connected. In additive manufacturing, various types of materials in powder, liquid or granular form are deposited in layers. As shown in FIG. 35, the deposited layers can be cured layer by layer until the entire component is complete. For example, an energized beam can be scanned over a bath of material to solidify a precise pattern of the material to form each layer until the entire component is complete. Similar techniques include, but are not limited to, rapid manufacturing, layered manufacturing, rapid prototyping, laser sintering, and electron beam melting.

It will be appreciated by those skilled in the art that changes could be made to the exemplary embodiments described above without departing from the broad inventive concept thereof. It is to be understood, therefore, that the subject disclosure is not limited to the particular exemplary embodiments disclosed, but it is intended to cover modifications within the spirit and scope of the subject disclosure as defined by the appended claims.

We claim:

1. An expandable intervertebral implant comprising:
a first endplate having:
a single continuous sloped anterior face of constant slope extending an overall height of the first endplate and located at an anterior end of the first endplate, and
a single continuous sloped posterior face of constant slope extending an overall height of the first endplate and located at a posterior end of the first endplate; and
a second endplate having a posteriorly facing sloped surface for slidably engaging the sloped anterior face of the first endplate,
wherein one of the first endplate and the second endplate moves relative to the other of the first endplate and the second endplate in an anterior-posterior direction when the first endplate slidingly engages the second endplate, and
wherein the first endplate moves in the anterior-posterior direction and in an inferior-superior direction simultaneously when the first endplate slidingly engages the second endplate.

2. The expandable intervertebral implant of claim 1, wherein the sloped anterior face slopes inwardly from a most superior end of the sloped anterior face to a most inferior end of the sloped anterior face.

3. The expandable intervertebral implant of claim 1, wherein the first endplate further comprises a track parallel to the sloped anterior face.

4. The expandable intervertebral implant of claim 3, wherein the second endplate further comprises a cooperating track for receiving the track of the first endplate.

5. The expandable intervertebral implant of claim 3, wherein the track is a female track.

6. The expandable intervertebral implant of claim 1, wherein the first endplate further comprises a sliding joint.

7. The expandable intervertebral implant of claim 6, wherein the second endplate further comprises a cooperating sliding joint for engaging the sliding joint of the first endplate.

8. The expandable intervertebral implant of claim 7, wherein the sliding joint of the first endplate is a female sliding joint and the cooperating sliding joint of the second endplate is a male sliding joint.

9. The expandable intervertebral implant of claim 7, wherein the sliding joint of the first endplate is a groove and the cooperating sliding joint of the second endplate is a tongue.

10. The expandable intervertebral implant of claim 1, wherein an angle of the sloped anterior face is substantially the same as an angle of the posteriorly facing sloped surface of the second endplate.

11. The expandable intervertebral implant of claim 1, wherein when the first endplate slidingly engages the second endplate, the first endplate moves in a vertical direction away from the second endplate.

12. The expandable intervertebral implant of claim 1, wherein the first endplate is movable between a first position and a second position relative to the second endplate, and in the first position, the sloped anterior face of the first endplate is substantially facing the posteriorly facing sloped surface of the second endplate and, in the second position, the sloped anterior face is anteriorly spaced from the posteriorly facing sloped surface.

13. The expandable intervertebral implant of claim 12, wherein in the second position, a majority of the sloped anterior face is anteriorly spaced from the posteriorly facing sloped surface of the second endplate.

14. The expandable intervertebral implant of claim 1, wherein the first endplate is movable between a first position and a second position relative to the second endplate, and in the first position, the first endplate is completely posterior to the posteriorly facing sloped surface of the second endplate.

15. The expandable intervertebral implant of claim 1, wherein the first endplate is substantially positioned posteriorly to the posteriorly facing sloped surface of the second endplate.

16. The expandable intervertebral implant of claim 1, wherein an anterior most end of the first endplate is spaced anteriorly from an entirety of the posteriorly facing sloped surface of the second endplate.

17. The expandable intervertebral implant of claim 1, wherein the sloped anterior face of the first endplate extends from the anterior-most end of the first endplate.

18. An expandable intervertebral implant comprising:
a first endplate that includes:
a single continuous sloped anterior face of constant slope extending an overall height of the first endplate and located at an anterior end of the first endplate that slopes inwardly from a most superior end of the sloped anterior face to a most inferior end of the sloped anterior face,
a single continuous sloped posterior face of constant slope extending an overall height of the first endplate and located at a posterior end of the first endplate, and
a groove track adjacent the sloped anterior face; and
a second endplate that includes:
a posteriorly facing sloped surface for slidably engaging the sloped anterior face of the first endplate, and
a tongue engaging the groove track;
wherein an angle of the posteriorly facing sloped surface is substantially the same as an angle of the sloped anterior face,
wherein one of the first endplate and the second endplate moves relative to the other of the first endplate and the second endplate in an anterior-posterior direction and an inferior-superior direction when the first endplate slidingly engages the second endplate, and wherein the first endplate is movable between a first position and a second position relative to the second endplate, and in the first position, the sloped anterior face of the first endplate is substantially facing the posteriorly facing sloped surface of the second endplate and is completely posterior to the posteriorly facing sloped surface, and in the second position, the sloped anterior face is anteriorly spaced from the posteriorly facing sloped surface.

* * * * *